US006897213B1

(12) United States Patent
Padia

(10) Patent No.: US 6,897,213 B1
(45) Date of Patent: May 24, 2005

(54) HETEROCYCLES AS CHOLECYSTOKININ (CCK) LIGANDS

(75) Inventor: Janak Khimchand Padia, Ypsilanti, MI (US)

(73) Assignee: Warner-Lambert Company, Morris Plains, NJ (US)

(*) Notice: Subject to any disclaimer, the term of this patent is extended or adjusted under 35 U.S.C. 154(b) by 0 days.

(21) Appl. No.: 08/812,508

(22) Filed: Mar. 7, 1997

Related U.S. Application Data

(63) Continuation of application No. 08/545,241, filed on Nov. 21, 1995, now abandoned, which is a continuation-in-part of application No. 08/364,624, filed on Dec. 27, 1997, now abandoned.

(51) Int. Cl.$^7$ ...................... C07D 239/95; A61K 31/517
(52) U.S. Cl. ............................... 514/234.5; 514/266.3; 544/116; 544/119; 544/287
(58) Field of Search ................. 544/287, 116, 544/119; 514/266.3, 234.5

(56) References Cited

U.S. PATENT DOCUMENTS

| | | | |
|---|---|---|---|
| 3,213,094 A | 10/1965 | Morgan | 360/251 |
| 3,217,005 A | 11/1965 | Kirchner | 260/256.4 |
| 3,322,766 A | 5/1967 | Schipper | 260/256.4 |
| 3,867,384 A | 2/1975 | Bullock et al. | 544/287 |
| 4,472,400 A | 9/1984 | Tully et al. | 514/212 |
| 4,547,504 A | 10/1985 | Fabre et al. | 514/255 |
| 4,826,528 A * | 5/1989 | Mengel et al. | 71/92 |
| 5,084,457 A | 1/1992 | Fanshawe et al. | 514/257 |
| 5,196,427 A | 3/1993 | Yu et al. | 514/259 |
| 5,204,354 A | 4/1993 | Chakravarty et al. | 514/259 |
| 5,276,038 A * | 1/1994 | Takasugi et al. | 514/259 |
| 5,278,316 A | 1/1994 | Horwell et al. | 548/496 |
| 5,354,755 A * | 10/1994 | Takasugi et al. | 514/259 |

FOREIGN PATENT DOCUMENTS

| | | |
|---|---|---|
| DE | 158549 | 1/1983 |
| GB | 2086903 | 11/1981 |
| WO | 94/26722 | 11/1994 |

OTHER PUBLICATIONS

Kottka et al., Chem. Abstract 104:207299, 1986.*
Liebowitz, PubMed Abstract (J Clin Psychiatry 58 Suppl 13:5–8), 1997.*
K. Kottke, et al., *Chemical Abstracts*, 1982, 96:69016j.
K. Kottke, et al., *Chemical Abstracts*, 1983, 99:70757v.
K. Kottke, et al., *Chemical Abstracts*, 1983, 99:158378h.
A.K.S. Gupta, et al., *Chemical Abstracts*, 1989, 111:52455g.
A–M.M.E. Omar, et al., *Eur J Med Chem—Chemica Therapeutica*, 1981, 16:1, 77–80.
K. Kottke, et al., *Chemical Abstracts*, 1983, 98:107241e.
K. Kottke, et al., *Chemical Abstracts*, 1978, 89:24242u.
16128u, *Chemical Abstracts*, vol. 78, 1973.
87715d, *Chemical Abstracts*, vol. 70, 1969.
140064s, *Chemical Abstracts*, vol. 82, 1975.
105:97416n, *Chemical Abstracts*, vol. 105, 1986.
96:142790p, *Chemical Abstracts*, vol. 96, 1982.
85:123860t, *Chemical Abstracts*, vol. 85, 1976.
"Intracerebroventricular Injections of Chlecystokinin Octapeptide Suppress Feeding, etc.", *Regulatory Peptides*, R.R. Schick, et al, 14 (1986) 277–291.
"Antinociceptive Action of Cholecystokinin Octapeptide, etc.", *Neuropharmacology*, R.G. Hill, et al, vol. 26, No. 4, pp. 289–300, 1986.
"Inhibition of Synaptic Transmission in the Hippocampus, etc.", *Brain Research*, Brian A. MacVicar, et al, 406 (1987) 130–135.
"Peptides, The Limbic Lobe and Schizophrenia", Gareth W. Roberts, et al, *Brain Research*, 288 (1983) 199–211.
"Cholecystokinin—Immunoreactive Boutons in Synaptic Contact, etc.", S.Totterdell and A.D. Smith, *Neuroscience*, vol. 19, No. 1 pp. 181–192, 1986.
"Opposite Actions of CCK–8 on Amphetamine–Induced Hyperlocomotion, etc.", F. Weiss, et al, *Pharmacology Biochemistry & Behavior*, vol. 30, pp. 3098,317 (1988).
"CCK–8 Modulation of Mesolimbic Dopamine: Antagonism of Amphetamine–Stimulated Behaviors", L.H. Schneider, et al, *Peptides*, vol. 4,pp. 749–753, 1983.
"Gastrointenstinal Hormones and Gastric Secrection", S.J.Konturek, *Gastrointestinal Hormones*, Ch.23, pp. 529–564 (1980) ed. G.B.J. Glass, Raven Press, NY.
"Role of Gastrin and Gastrin Receptors on the Growth of a Transplantable Mouse Colon Carcinoma, etc.", *Cancer Research 44*, 1612–1616, Apr., 1986.
"Effects of Gastrin, Proglumide, and Somatostatin on Growth of Human Colon Cancer", *Gastroenterology* 1988; 95: 1541–8.
"The Physiology of Cholecystokinin in Brain and Gut", G.J. Dockray, *British Medical Bulletin* (1982) vol. 38, No. 3, pp. 253–258.
"The Neuroendocrine Control of Appetite, etc.", John E. Morley, *Life Sciences*, vol. 27, pp. 355–368 (1980).
"Immunochemical Evidence of Cholecystokinin Tetrapeptides in Hog Brain", Rehfeld and Gotterman, *Journal of Neurochemistry*, vol. 32, pp. 1339–1341.
"Cholecystokinin Octapeptide: Continuous Picomole Injections, etc.", Della–Fera and Baile, *Science*, vol. 26, pp. 471–473 (1979).

(Continued)

*Primary Examiner*—Deepak Rao
(74) *Attorney, Agent, or Firm*—Mehdi Ganjaizadeh; Charles W. Ashbrook; Michael Atkins

(57) ABSTRACT

Novel quinazolinone derivatives with good binding affinity for the CCK-A and CCK-B receptors, pharmaceutical compositions containing them and methods of using them are taught. The compounds are useful agents to suppress appetite, reduce gastric acid secretion, and the like.

12 Claims, No Drawings

OTHER PUBLICATIONS

"Heterogeneity of GABAergic Cells In Cat Visual Cortex", H.Demeulemeester, et al, *The Journal of Neuroscience*, Mar. 1988 (8(3):988–1000.
"Hypnotics and Sedatives", Stewart C. Harvey, *The Pharmacological Basis of Therapeutics*, 1985, pp. 339–371.
"Synthesis and some reactions of 3–phenyl(1H, 3H)–quinazoline–2–thione–4–one", El–Deen and El–Desuky, *J.Serb.Chem.Soc.* 57(11)719–723 (1992).
"Synthesis and Anticonvulsant Activity of Some New 2–Substituted 3–Aryl–4(3H)–quinazolinones", James F. Wolfe, et al *J.Med.Chem.* 1990, 33, pp. 161–166.
"Synthesis of the 1,2,4–Triazolo[4,3–a] quinazol in–5–ones and Related Compounds", H.A. El–Sherief, et al *Bull.Chem. Soc.Jpn.*, 56, 1227–1230 (1983).
"Synthesis and Pesticidal Activity of some Quinazol in–4(3H)–one Derivatives," Gupta & Pandey, *Pestic.Sci.* 26, 1989, 41–49.
"Synthesis of some novel quinazolone thiosemicarbazide and thiazoline derivatives for potential anti–microbial activity", Omar, et al, *Eur.J.Med.Chem.—Chemica Therapeutica*, Jan.–Feb., 1981–16, No. 1, pp. 77–80.
94:175041, *Chemical Abstracts*, vol. 94, 1981.
94:132238j, *Chemical Abstracts*, vol. 94, 1981.
99:158378h, *Chemical Abstracts*, vol. 99, 1983.
111:52455g, *Chemical Abstracts*, vol. 111, 1989.
89(15):1294696, *Chemical Abstracts*, 1978.
95(1):7198r, *Chemical Abstracts*, 1980.
98(23):198151q, *Chemical Abstracts*, 1983.
*Chemical Abstracts*, Reg. No. 146849–71–0.
*Chemical Abstracts*, Reg. No. 121828–87–3.
*Chemical Abstracts*, Reg. No. 121678–90–8.
*Chemical Abstracts*, Reg. No. 121662–01–9.
*Chemical Abstracts*, Reg. No. 121662–00–8.
*Chemical Abstracts*, Reg. No. 121661–99–2.
*Chemical Abstracts*, Reg. No. 121661–98–1.
*Chemical Abstracts*, Reg. No. 121661–97–0.
*Chemical Abstracts*, Reg. No. 121661–96–9.
*Chemical Abstracts*, Reg. No. 121661–95–8.
*Chemical Abstracts*, Reg. No. 121661–94–7.
*Chemical Abstracts*, Reg. No. 121661–93–6.
*Chemical Abstracts*, Reg. No. 121661–92–5.
*Chemical Abstracts*, Reg. No. 121661–91–4.
*Chemical Abstracts*, Reg. No. 121661–90–3.
*Chemical Abstracts*, Reg. No. 101164–48–1.
*Chemical Abstracts*, Reg. No. 87466–11–3.
*Chemical Abstracts*, Reg. No. 87466–10–2.
*Chemical Abstracts*, Reg. No. 87466–09–9.
*Chemical Abstracts*, Reg. No. 87466–08–8.
*Chemical Abstracts*, Reg. No. 87466–07–7.
*Chemical Abstracts*, Reg. No. 87466–06–6.
*Chemical Abstracts*, Reg. No. 86842–56–0.
*Chemical Abstracts*, Reg. No. 86842–47–9.
*Chemical Abstracts*, Reg. No. 86662–55–7.
*Chemical Abstracts*, Reg. No. 86513–40–8.
*Chemical Abstracts*, Reg. No. 86507–00–8.
*Chemical Abstracts*, Reg. No. 86506–99–2.
*Chemical Abstracts*, Reg. No. 86506–98–1.
*Chemical Abstracts*, Reg. No. 86506–97–0.
*Chemical Abstracts*, Reg. No. 86506–96–9.
*Chemical Abstracts*, Reg. No. 86506–95–8.
*Chemical Abstracts*, Reg. No. 86506–94–7.
*Chemical Abstracts*, Reg. No. 85784–60–7.
*Chemical Abstracts*, Reg. No. 85773–55–3.
*Chemical Abstracts*, Reg. No. 85773–54–2.
*Chemical Abstracts*, Reg. No. 85773–53–1.
*Chemical Abstracts*, Reg. No. 85773–52–0.
*Chemical Abstracts*, Reg. No. 85773–51–9.
*Chemical Abstracts*, Reg. No. 85773–50–8.
*Chemical Abstracts*, Reg. No. 85773–49–5.
*Chemical Abstracts*, Reg. No. 85773–48–4.
*Chemical Abstracts*, Reg. No. 85773–47–3.
*Chemical Abstracts*, Reg. No. 85773–46–2.
*Chemical Abstracts*, Reg. No. 85773–45–1.
*Chemical Abstracts*, Reg. No. 85773–44–0.
*Chemical Abstracts*, Reg. No. 85773–43–9.
*Chemical Abstracts*, Reg. No. 85773–42–8.
*Chemical Abstracts*, Reg. No. 85773–41–7.
*Chemical Abstracts*, Reg. No. 85773–40–6.
*Chemical Abstracts*, Reg. No. 85773–39–3.
*Chemical Abstracts*, Reg. No. 85773–38–2.
*Chemical Abstracts*, Reg. No. 85773–11–1.
*Chemical Abstracts*, Reg. No. 85773–10–0.
*Chemical Abstracts*, Reg. No. 85773–09–7.
*Chemical Abstracts*, Reg. No. 77775–32–7.
*Chemical Abstracts*, Reg. No. 77747–39–8.
*Chemical Abstracts*, Reg. No. 77747–38–7.
*Chemical Abstracts*, Reg. No. 77747–37–6.
*Chemical Abstracts*, Reg. No. 77747–36–5.
*Chemical Abstracts*, Reg. No. 77437–24–2.
*Chemical Abstracts*, Reg. No. 77437–23–1.
*Chemical Abstracts*, Reg. No. 77437–22–0.
*Chemical Abstracts*, Reg. No. 77437–21–9.
*Chemical Abstracts*, Reg. No. 77437–20–8.
*Chemical Abstracts*, Reg. No. 77437–19–5.
*Chemical Abstracts*, Reg. No. 77437–18–4.
*Chemical Abstracts*, Reg. No. 77437–17–3.
*Chemical Abstracts*, Reg. No. 77437–16–2.
*Chemical Abstracts*, Reg. No. 77437–15–1.
*Chemical Abstracts*, Reg. No. 77437–14–0.
*Chemical Abstracts*, Reg. No. 77437–13–9.
*Chemical Abstracts*, Reg. No. 77437–12–8.
*Chemical Abstracts*, Reg. No. 77437–11–7.
*Chemical Abstracts*, Reg. No. 77437–10–6.
*Chemical Abstracts*, Reg. No. 77437–09–3.
*Chemical Abstracts*, Reg. No. 77437–08–2.
*Chemical Abstracts*, Reg. No. 77437–07–1.
*Chemical Abstracts*, Reg. No. 77437–06–0.
*Chemical Abstracts*, Reg. No. 77066–23–0.
*Chemical Abstracts*, Reg. No. 77066–22–9.
*Chemical Abstracts*, Reg. No. 77066–21–8.
*Chemical Abstracts*, Reg. No. 77066–20–7.
*Chemical Abstracts*, Reg. No. 77066–19–4.
*Chemical Abstracts*, Reg. No. 67443–12–3.
*Chemical Abstracts*, Reg. No. 67443–11–2.
*Chemical Abstracts*, Reg. No. 67443–10–1.
*Chemical Abstracts*, Reg. No. 67443–09–8.
*Chemical Abstracts*, Reg. No. 67443–08–7.
*Chemical Abstracts*, Reg. No. 67443–07–6.
*Chemical Abstracts*, Reg. No. 67443–06–5.
*Chemical Abstracts*, Reg. No. 67443–05–4.
*Chemical Abstracts*, Reg. No. 67443–04–3.
*Chemical Abstracts*, Reg. No. 67443–03–2.
"Effect of Gastrointestinal Hormones on Growth of Gastrointestinal Tissue", L. R. Johnson, *Gastrointestinal Hormones*, pp. 507–527, 1980.
"Gastrinomas", Fl. Stadil, *Gastrointestinal Hormones*, pp. 729–739, 1980.

*Cholecystokinin: Isolation, Structure and Functions,* G.B.J. Glass, Ed., Raven Press, New York, 1980, pp. 169–221.
*Cholecystokinin in the Nervous System,* J. de Belleroche and G.J. Dockray, Ed., Ellis Horwood, Chichester, England (1984) pp. 110–127.

*TIPS* 11:271–273 (1990).

Woodruff G.N. and Hughes J., *AnnRev. Pharmacol. and Toxicol.,* 31:469–501 (1991).

* cited by examiner

HETEROCYCLES AS CHOLECYSTOKININ (CCK) LIGANDS

CROSS REFERENCE TO RELATED APPLICATION

This application is a continuation of application Ser. No. 08/545,241 filed Nov. 21, 1995 now abandoned which is a continuation-in-part of application Ser. No. 08/364,624 filed Dec. 27, 1994 now abandoned.

TECHNICAL FIELD

The invention pertains to quinazoline materials. In particular, the invention is concerned with central cholecystokinin (CCK) antagonists and, in particular, the materials that have a binding affinity for the CCK-B receptor.

BACKGROUND ART

Cholecystokinin is structurally and functionally related to gastrin. The active C-terminal tetra-peptide amide of gastrin is duplicated in cholecystokinin. The major structural difference that dictates whether a peptide of the CCK-gastrin family has a gastrin-like or CCK-like pattern of activity is the position of the tyrosyl residue and whether or not it is sulfated. Gastrointestinal Hormones, edited by George B. Jerzy, Glass Raven Press, New York, 1980, pp. 512–513. CCK is a polypeptide which was originally isolated from the gut. Later investigations, however, discovered CCK is also localized in the mammalian central nervous system; particularly high levels of the octapeptide form (CCK-8) are found in hippocampus. Immunocytochemical staining has revealed that CCK-8 containing neurons appear to be interneurons in the hippocampus. "Inhibition of Synaptic Transmission in the Hippocampus by Cholecystokinin (CCK) and its Antagonism by a CCK Analog ($CCK_{27-33}$)" (Elsevier, B. A. MacVicar, J. P. Kerrin and J. S. Davison, Basic Research 406: 130–135, 1987).

Agents acting at central cholecystokinin (CCK) receptors may induce satiety (Schick, Yaksh, and Go, Regulatory Peptides 14:277–291, 1986). They are also expected to act as analgesics (Hill, Hughes and Pittaway, Neuropharmacology 26:289–300, 1987), and as anticonvulsants (Macvicar, Kerrin, and Davison, Brain Research 406:130–135, 1987).

Reduced levels of CCK-peptides have been found in the brains of schizophrenic patients compared with controls (Robers, Ferrier, Lee, Crow, Johnstone, Owens, Bacarese-Hamilton, McGregor, O'Shaughnessey, Polak, and Bloom, Brain Research 288:199–211, 1983). It has been proposed that changes in the activity of CCK neurones projecting to the nucleus accumbens may play a role in schizophrenic processes by influencing dopaminergic function (Totterdell and Smith, Neuroscience 19:181–192, 1986). This is consistent with numerous reports that CCK peptides modulate dopaminergic function in the basal ganglia and particularly the nucleus accumbens (Weiss, Tanzer, and Ettenberg, Pharmacology, Biochemistry and Behaviour 30:309–317, 1998; Schneider, Allpert, and Iversen, Peptides 4:749–753, 1983). It may therefore be expected that agents modifying CCK receptor activity may have therapeutic value in conditions associated with disturbed function of central dopaminergic function such as schizophrenia and Parkinson's disease.

CCK and gastrin peptides share a common carboxy terminal pentapeptide sequence, and CCK peptides can bind to the gastrin receptor of the stomach mucosa and elicit acid secretion in many species including human (Kontruek, Gastrointestinal Hormones, Ch. 23, pp. 529–564, 1980, ed. G. B. J. Glass, Raven Press, NY). The receptors for CCK have been classified into two subtypes according to their affinity for CCK fragments and their analogs. CCK-A receptors are found predominantly in peripheral tissues such as pancreas and gall bladder. They have high affinity for the sulfated octapeptide (CCK-8S) and lower affinity for the corresponding desulfated fragment CCK-8d, CCK-4 and gastrin. Conversely, CCK-B receptors are widely distributed through-out the brain and exhibit high affinity for CCK-8s, CCK-4 and gastrin. (Innis, R. B.; Synder, S. H., Proc. Natl. Acad. Sci. USA, 77:6917–6921, 1980 and Moran, T. H.; Robinson, P.; Goldrich, M. S.; McHugh, P., Brain Research, 362: 175–179, 1989). Antagonists of the CCK-B receptor would also be expected to be antagonists at the stomach gastrin receptor, and this would also be of value for conditions involving excessive acid secretion.

CCK and gastrin peptides have trophic effects on the pancreas and various tissues of the gastrointestinal tract (Johnson, Gastrointestinal Hormones, edited by George B. Jerzy Glass, "Effect of Gastrointestinal Hormones on Growth of Gastrointestinal Tissue," Chapter 22, pp. 507–527), actions which are associated with increased DNA and RNA synthesis. Moreover, gastrin secreting cells are associated with certain gastrointestinal tumors as in the Zollinger-Ellison syndrome (Stadil, Gastrointestinal Hormones, edited by George B. Jerzy Glass, "Gastrinomas," Chapter 30, pp. 729–739), and some colorectal tumors may also be gastrin/CCK dependent (Singh, Walker, Townsend, and Thompson, Cancer Research 46:1612, 1986; Smith, J. P., Gastroenterology 95:1541, 1988). Antagonists of CCK/gastrin receptors could therefore be of therapeutic value as antitumor agents.

The CCK peptides are widely distributed in various organs of the body including the gastrointestinal tract, endocrine glands, and the nerves of the peripheral and central nervous systems. Various biologically active forms have been identified including a 33-amino acid hormone and various carboxylterminus fragments of this peptide (e.g., the octapeptide CCK26–33 and the tetrapeptide CCK30–33). (G. J. Dockray, Br. Med. Bull. 38 (3):253–258, 1982).

The various CCK peptides are thought to be involved in the control of smooth muscle contractility, exocrine and endocrine gland secretion, sensory nerve transmission, and numerous brain functions. Administration of the native peptides cause gall bladder contraction, amylase secretion, excitation of central neurons, inhibition of feeding, anticonvulsive actions and other behavioral effects. (Cholecystokinin: Isolation, Structure and Functions, G. B. J. Glass, Ed., Raven Press, New York, 1980, pp. 169–221; J. E. Morley, Life Sciences 27:355–368, 1980; Cholecystokinin in the Nervous System, J. de Belleroche and G. J. Dockray, Ed., Ellis Horwood, Chichester, England, 1984, p. 110–127).

The high concentrations of CCK peptides in many brain areas also indicate major brain functions for these peptides (G. J. Dockray, Br. Med. Bull, 38 (3):253–258, 1982). The most abundant form of brain CCK found is CCK 26–33, although small quantities of CCK 30–33 exist (Rehfeld and Gotterman, J. Neurochem. 32:1339–1341, 1979). The role of central nervous system CCK is not known with certainty, but it has been implicated in the control of feeding (Della-fera and Baile, Science 206:471–473, 1979).

Currently available appetite suppressant drugs either act peripherally, by increasing energy expenditure (such as thyroxine), or in some other manner (such as the biguanides), or act by exerting a central effect on appetite or satiety.

Centrally acting appetite suppressants either potentiate central catecholamine pathways and tend to be stimulants (for example, amphetamine), or influence serotonergic pathways (for example, fenfluramine). Other forms of drug therapy include bulking agents which act by filling the stomach, thereby inducing a "feeling" of satiety.

CCK is known to be present in some cortical interneurones which also contain gamma-aminobutyric acid (GABA) (H. Demeulemeester et al., *J. Neuroscience* 8:988–1000, 1988). Agents that modify GABA action may have utility as anxiolytic or hypnotic agents (S. C. Harvey, *The Pharmacological Basis of Therapeutics* (7th ed.) 1985, pp. 339–371, MacMillan). Thus, agents which modify CCK action may have parallel anxiolytic or hypnotic activities. The role of CCK in anxiety is disclosed in *TIPS* 11:271–273, 1990, and is fully detailed in Woodruff, G. N. and Hughes, J., 1991, *Ann. Rev. Pharmacol and Toxicol.* 31, 469–501.

Since the identification in brain extracts of the carboxyl (C)-terminal octapeptide of CCK-8, much evidence has arisen to suggest that CCK-related peptides have neuroregulatory roles in the central nervous system (CNS) in addition to their well-known hormonal functions in controlling digestion. *The Physiology of Cholecystokinin in Brain and Gut*, British Medical Bulletin (1982) Vol. 38, No. 3, pp. 353–358, by G. J. Dockray.

It is an object of the present invention to described pharmaceutical compositions that are effective to suppress the appetite in a mammal.

It is another object of the present invention to describe compositions that are effective to reduce gastric acid secretion in a mammal.

It is yet another object of the present invention to describe compositions useful to effect a reduction of anxiety in a mammal.

It is still another object of the present invention to describe compositions useful to effectively treat gastrointestinal ulcers in a mammal.

It is another object of the present invention to describe compositions useful to effectively treat psychotic behavior in a mammal.

Still further, it is an object of the present invention to describe compositions useful to effectively block the reaction caused by withdrawal from drug or alcohol use in a mammal.

It is still a further object of the present invention to describe compositions useful to effectively potentiate the affects of morphine and other opioids in treating pain in a mammal.

It is yet another object of the present invention to describe compositions useful to effectively treat and/or prevent panic in a mammal.

It is an object of the present invention to describe compositions which can be radio labeled and are useful for effecting diagnosis of gastrine-dependent tumors in a mammal.

SUMMARY OF THE INVENTION

The invention relates to compounds of Formula

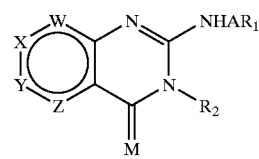

Formula I wherein W, X, Y and Z are each independently selected from C—$R_3$, C—$R_4$, C—$R_5$, C—$R_6$ and N (nitrogen) and that no more than two of W, X, Y and Z are N;

wherein $R_3$, $R_4$, $R_5$ and $R_6$ are each independently hydrogen, hydroxy, sulfhydryl, lower alkoxy (1–4 carbon atoms), lower thioalkoxy (1–4 carbon atoms), lower alkyl (1–4 carbon atoms), halo, CN, $CF_3$, $NO_2$, $COOR_7$ or $NR_7R_8$;

wherein $R_7$ and $R_8$ are independently hydrogen or lower alkyl (1–4 carbon atoms);

M is oxygen or sulfur;

A is selected from the group consisting of:

(i)

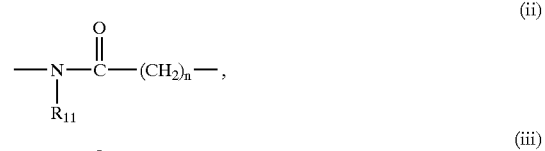

(ii)

(iii)

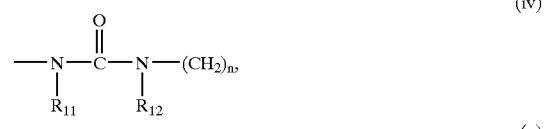

(iv)

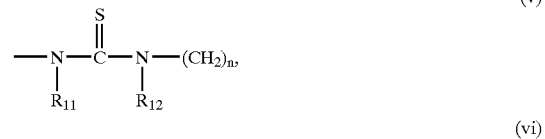

(v)

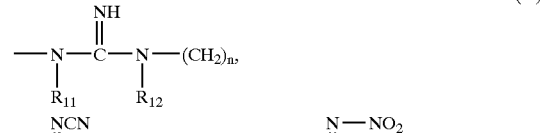

(vi)

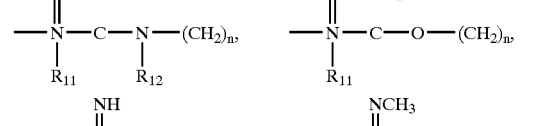

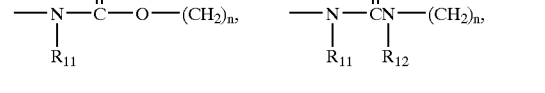

-continued $$-N(R_{11})-C(=N-NO_2)-N(R_{12})-(CH_2)_n,\quad -N(R_{11})-C(=O)-N(R_{12})-SO_2(CH_2)_n,$$

$$-N(R_{11})-C(=S)-(CH_2)_n,\quad -N(R_{11})-S(=O)_2-N(R_{12})-(CH_2)_n,$$

$$-N(R_{11})-C(=S)-N(R_{12})-SO_2(CH_2)_n-,\quad -O-C(=O)-N(R_{11})-(CH_2)_n,$$

$$-O-S(=O)_2-N(R_{11})-(CH_2)_n,\quad -O-C(=O)-(CH_2)_n,$$

$$-O-C(=S)-N(R_{11})-(CH_2)_n,\quad -O-C(=O)-O(CH_2)_n,$$

$$-O-C(=S)-(CH_2)_n,\quad \text{and}\quad -O-(CH_2)_n,$$

wherein $R_{11}$ and $R_{12}$ are independently hydrogen or lower alkyl (1–4 carbon atoms); n=0 or 1;

$R_1$ and $R_2$ independently are: an alkyl of 1 to 6 carbon atoms, unsubstituted, mono or polysubstituted phenyl or polyaromatic, unsubstituted, mono or polysubstituted heteroaromatic, with hetero atom(s) N (nitrogen), O (oxygen) and/or S (sulfur) or, unsubstituted, mono or polysubstituted aralkyl, unsubstituted, mono or polysubstituted cyclo or polycycloalkyl hydrocarbon, or mono or polyheterocycle (3 to 8 atoms per ring) with one to four hetero atoms as N (nitrogen), O (oxygen) or S (sulfur); and wherein the substitutions are selected from
hydrogen
lower alkyl of 1–4 carbon atoms,
$(CH_2)_iOR_{13}$
$(CH_2)_iSR_{13}$
trifluoromethyl
nitro
halo
cyano
azido
acetyl $$\left(-C(R_{16})(R_{15})-\right)_i-COOR_{13}\quad \left(-C(R_{16})(R_{15})-\right)_i-CONR_{13}R_{14}$$

$$\left(-C(R_{16})(R_{15})-\right)_i-NR_{13}R_{14}\quad \left(-C(R_{16})(R_{15})-\right)_i-CONHSO_2R_{13}$$

$(CH_2)_iOC(O)R_{13}$ $$\left(-C(R_{16})(R_{15})-\right)_i-S(O)_jR_{13}\quad \left(-C(R_{16})(R_{15})-\right)_i-S(O)_jNR_{13}R_{14}$$

$(CH_2)_i$-tetrazole
polyhydroxy alkyl or cycloalkyl of from 5 to 8 carbon atoms, wherein i and j are independently 0, 1, 2, and $R_{13}$, $R_{14}$, $R_{15}$, $R_{16}$ are each independently hydrogen, lower alkyl, alkaryl of from 7 to 10 carbon atoms;

$NR_{13}R^{14}$ is also mono or bicyclic ring with one to four hetero atoms as N,O,S;

provided that when W, X, Y and Z are each $C-R_3$, $C-R_4$, $C-R_5$ and $C-R_6$ and $R_3$, $R_4$, $R_5$ and $R_6$ are hydrogen and A is $$-NH-C(=O)-\quad \text{and}$$

$R_1$ is unsubstituted phenyl, then $R_2$ cannot be unsubstituted phenyl;

further provided that when W, X, Y and Z are each $C-R_3$, $C-R_4$, $C-R_5$, and $C-R_6$ and $R_3$, $R_4$, $R_5$ and $R_6$ are hydrogen or halogen and A is $$-NH-C(=O)-NH-,$$

and
M is oxygen, and
$R_2$ is unsubstituted or mono substituted phenyl and wherein substitution is chloro, bromo, butyl, n-butoxy, iso-butoxy, then $R_1$ cannot be unsubstituted or mono substituted phenyl, or unsubstituted naphthyl wherein substitution is chloro or bromo;

furthermore provided that when W, X, Y and Z are each $C-R_3$, $C-R_4$, $C-R_5$, and $C-R_6$ and $R_3$, $R_4$, $R_5$ and $R_6$ are hydrogen or halogen and A is $$-NH-C(=S)-NH-,$$

and
M is oxygen, and
$R_1$ is unsubstituted phenyl, unsubstituted benzyl, unsubstituted naphthyl or mono substituted phenyl wherein substitution is halogen, methyl, n-butyl or methoxy, then $R_2$ cannot be: a) unsubstituted phenyl; b) unsubstituted naphthyl; c) unsubstituted benzyl; d) mono substituted phenyl wherein substitution is halogen, methyl, n-butoxy, iso-butoxy, or methoxy; or e) disubstituted phenyl wherein substitution is methyl.

The invention relates to a method for treating a condition advantageously affected by the binding of a compound of Formula I (as defined above) to a CCK receptor in a mammal in need of such treatment comprising providing an effective binding amount of the compound of Formula I (as defined above) and a pharmaceutically acceptable salt thereof to such patient.

The invention is also concerned with utilizing the composition of Formula I in an effective amount to suppress the appetite in a mammal.

The invention is also concerned with using the compound of Formula I to reduce the gastric acid secretion in a mammal.

The invention is also concerned with the composition of Formula I to reduce anxiety in a mammal.

The invention is also concerned with using the composition of Formula I to treat gastro intestinal ulcers in a mammal.

The invention is also concerned with the composition of Formula I used to treat psychotic behavior in a mammal.

The invention is also concerned with utilizing the composition of Formula 0 to block the reaction caused by withdrawal from a drug or alcohol use in a mammal.

The invention is also concerned with utilizing the composition of Formula I to potentiate the effects of morphine and other opioids in treating pain.

The invention is also concerned with utilizing the composition of Formula I to treat and/or prevent panic in a mammal.

The invention is also concerned with utilizing the composition of Formula I as a diagnostic tool for gastrine dependent tumors in a mammal by utilizing a radio labeled iodo compound of Formula I.

DESCRIPTION OF PREFERRED EMBODIMENTS

The compounds of Formula I are as follows:

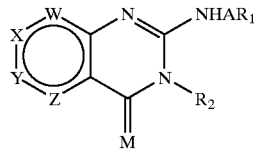

Formula I wherein W, X, Y and Z are each independently selected from C—$R_3$, C—$R_4$, C—$R_5$, C—$R_6$ and N (nitrogen) and that no more than two of W, X, Y and Z are N;

wherein $R_3$, $R_4$, $R_5$ and $R_6$ are each independently hydrogen, hydroxy, sulfhydryl, lower alkoxy (1–4 carbon atoms), lower thioalkoxy (1–4 carbon atoms), lower alkyl (1–4 carbon atoms), halo, CN, $CF_3$, $NO_2$, $COOR_7$ or $NR_7R_8$;

wherein $R_2$ and $R_8$ are independently hydrogen or lower alkyl (1–4 carbon atoms);

M is oxygen or sulfur;

A is selected from the group consisting of:

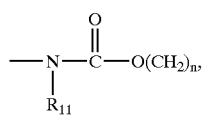

(i)

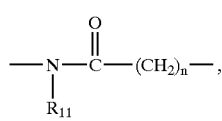

(ii)

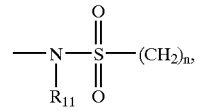

(iii)

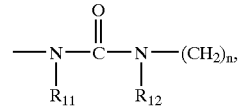

(iv)

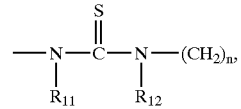

(v)

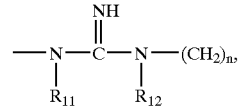

(vi)

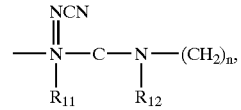 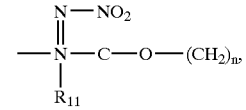

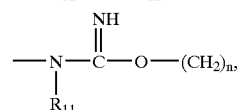 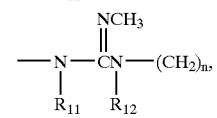

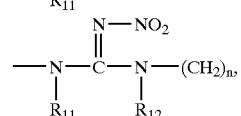 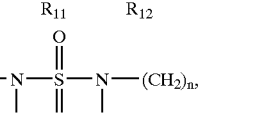

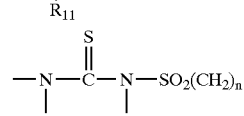 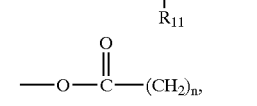

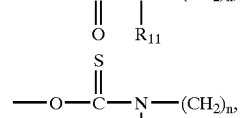 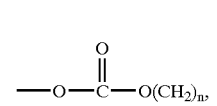

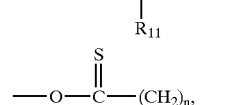

wherein $R_{11}$ and $R_{12}$ are independently hydrogen or lower alkyl (1–4 carbon atoms); n=0 or 1;

$R_1$ and $R_2$ independently are:

an alkyl of 1 to 6 carbon atoms, unsubstituted, mono or polysubstituted phenyl or polyaromatic, unsubstituted, mono or polysubstituted heteroaromatic, with hetero atom(s) N (nitrogen), O (oxygen) and/or S (sulfur) or, unsubstituted, mono or polysubstituted aralkyl, unsubstituted, mono or polysubstituted cyclo or polycycloalkyl hydrocarbon, or mono or polyheterocycle (3 to 8 atoms per ring) with one to four hetero atoms as N (nitrogen), O (oxygen) or S (sulfur); and wherein the substitutions are selected from
hydrogen
lower alkyl of 1–4 carbon atoms,
$(CH_2)_iOR_{13}$
$(CH_2)_iSR_{13}$
trifluoromethyl
nitro
halo
cyano
azido
acetyl

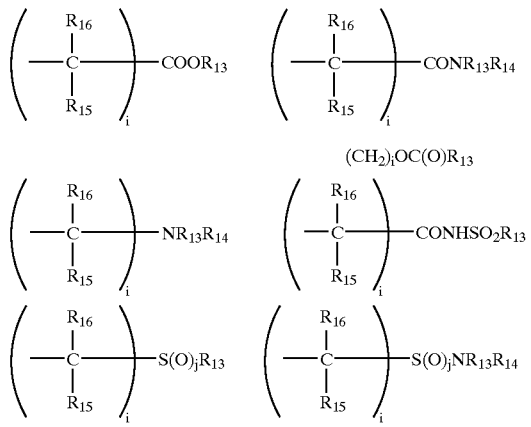

$(CH_2)_i$-tetrazole
polyhydroxy alkyl or cycloalkyl of from 5 to 8 carbon atoms,
wherein i and j are independently 0, 1, 2, and $R_{13}$, $R_{14}$, $R_{15}$, $R_{16}$ are each independently hydrogen, lower alkyl, alkaryl of from 7 to 10 carbon atoms;
$NR_{13}R_{14}$ is also mono or bicyclic ring with one to four hetero atoms as N,O,S;
provided that when W, X, Y and Z are each C—$R_3$, C—$R_4$, C—$R_5$ and C—$R_6$ and $R_3$, $R_4$, $R_5$ and $R_6$ are hydrogen and
A is

and $R_1$ is unsubstituted phenyl, then $R_2$ cannot be unsubstituted phenyl;
further provided that when W, X, Y and Z are each C—$R_3$, C—$R_4$, C—$R_5$, and C—$R_6$ and $R_3$, $R_4$, $R_5$ and $R_6$ are hydrogen or halogen and
A is

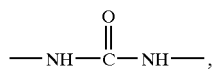

and
M is oxygen, and
$R_2$ is unsubstituted or mono substituted phenyl and wherein substitution is chloro, bromo, butyl, n-butoxy, iso-butoxy, then $R_1$ cannot be unsubstituted or mono substituted phenyl, or unsubstituted naphthyl wherein substitution is chloro or bromo;
furthermore provided that when W, X, Y and Z are each C—$R_3$, C—$R_4$, C—$R_5$, and C—$R_6$ and $R_3$, $R_4$, $R_5$ and $R_6$ are hydrogen or halogen and A is

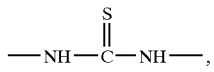

and
M is oxygen, and
$R_1$ is unsubstituted phenyl, unsubstituted benzyl, unsubstituted naphthyl or mono substituted phenyl wherein substitution is halogen, methyl or methoxy, then $R_2$ cannot be: a) unsubstituted phenyl; b) unsubstituted naphthyl; c) unsubstituted benzyl; d) mono substituted phenyl wherein substitution is halogen, methyl, n-butoxy, iso-butoxy, or methoxy; or e) disubstituted phenyl wherein substitution is methyl.

Preferred compounds of the instant invention are those of Formula I,
wherein:
W and Y are each independently C—$R_3$, C—$R_5$ or N,
X and Z are each independently C—$R_4$ or C—$R_6$,
wherein $R_3$, $R_4$, $R_5$ and $R_6$ are each independently chlorine, bromine, iodine, carbmethoxy, carboxy, methoxy, methyl, thio, thiomethyl, thioethyl, and hydroxy;
M is O or S;
A is selected from

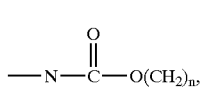 (i)

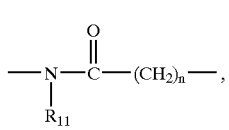 (ii)

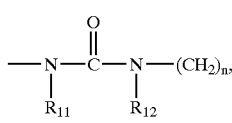 (iii)

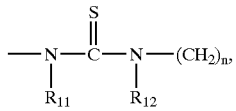 (iv)

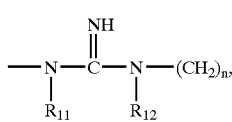 (vi)

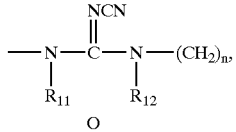

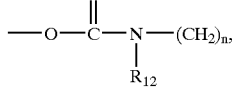

wherein $R_{11}$, and $R_{12}$ are independently hydrogen or alkyl of from 1 to 4 carbon atoms, n is 0 or 1;
$R_1$ and $R_2$ are independently an unsubstituted, mono or polysubstituted phenyl,
pyridyl,
pyrrolyl,
furanyl,
thiofuranyl,
pyrimidinyl,
indolyl,
quinolinyl,
quinaxolinyl; or
a cyclo or polycycloalkyl hydrocarbon of 6 to 12 carbon atoms;
  wherein the substituents are indicated above, preferably up to three substituents.
  Preferred substituents are:
$R_{13}$ and $R_{14}$ are each independently hydrogen, methyl, ethyl, t-butyl, i-propyl, benzyl,
$R_{15}$ and $R_{16}$ are each independently methyl,
$NR_{13}R_{14}$ is also selected from:

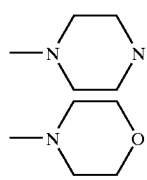 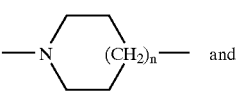 and

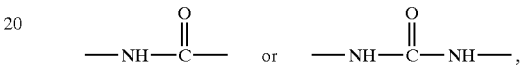

where $R_{17}$ is alkyl of 1 to 3 carbon atoms.
More preferred compounds of the instant invention are those of Formula I, wherein:
  W is C—$R_3$ or N wherein $R_3$ is selected from hydrogen, chlorine, bromine, iodine, methoxy, and methyl;
  X is C—$R_4$ wherein $R_4$ is selected from hydrogen, chlorine, hydroxy, methoxy, sulfhydryl and thioethylether;
  Y is C—$R_5$ wherein $R_5$ is selected from hydrogen, chlorine, bromine, iodine, methoxy, methyl, carboxy, and carbmethoxy;
  Z is C—$R_6$ and N, wherein $R_6$ is hydrogen;
  M is oxygen or sulfur;
  A is selected from

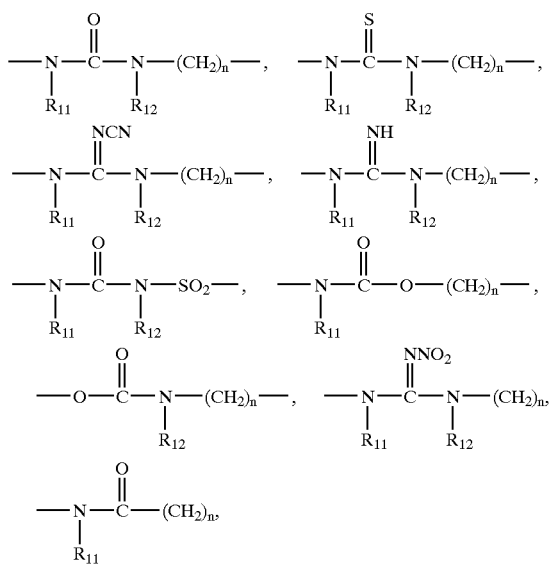

wherein $R_{11}$ and $R_{12}$ are hydrogen;
n is 0 or 1;
$R_1$ and $R_2$ are independently phenyl,
mono or polysubstituted phenyl,
pyridyl,
pyrrolyl,
furanyl,
thiofuranyl,
pyrimidinyl,
indolyl,
quinolinyl,
quinaxolinyl;
  wherein substitutions are the same as above.
  Another preferred class of compounds is that of Formula I wherein:
M is sulfur,
A is

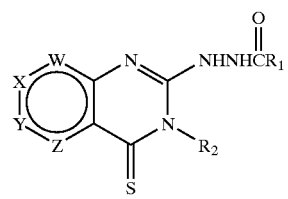

and W, X, Y, Z, $R_1$ and $R_2$ are as defined above. See structures A and B.

Structure A

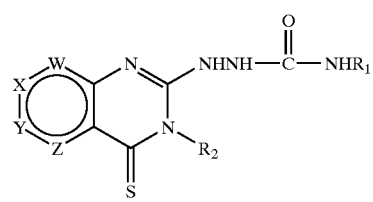

Structure B

Another preferred class of compounds is that of Formula I wherein:
M is oxygen;
A is

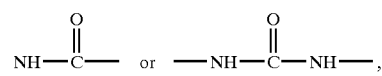

W, X, Y, and Z are selected from C—$R_3$, C—$R_4$, C—$R_5$, C—$R_6$ and N and at least one and no more than two of W, X, Y and Z are N. $R_1$, $R_2$, $R_3$, $R_4$, $R_5$ and $R_6$ are as defined above. See Structures C and D.

Structures C & D

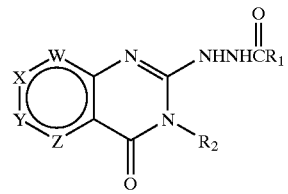

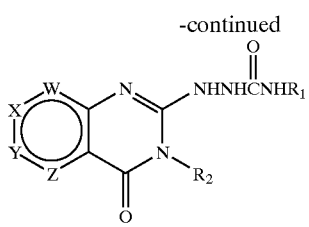

Another preferred class of compounds is that of Structure E:

Structure E

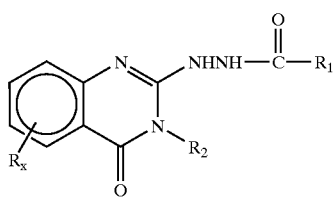

wherein $R_x$ is hydroxy, sulfhydryl, lower alkoxy (1–4 carbon atoms), lower thioalkoxy (1–4 carbon atoms), lower alkyl (1–4 carbon atoms), halo, CN, $CF_3$, $NO_2$, $COOR_7$ or $NR_7R_8$, where x=0–3;

wherein $R_7$ and $R_8$ are independently hydrogen or lower alkyl (1–4 carbon atoms);

$R_1$ and $R_2$ are as defined in Formula I.

Another preferred class of compounds is that of Formula I wherein W, X, Y and Z are selected from C—$R_3$, C—$R_4$, C—$R_5$ and C—$R_6$;

M is oxygen;

A is

$R_1$ and $R_2$ cannot both be phenyl in the same compound; and $R_3$, $R_4$, $R_5$ and $R_6$ are as defined above. See Structures F and G.

Structures F & G

F

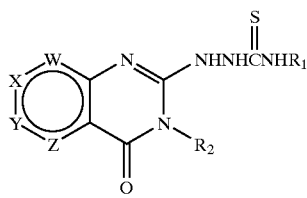

G (second structure)

Another preferred class of compounds is that of Formula 1 wherein:

M is S (sulfur);

W, X, Y, Z, $R_1$ and $R_2$ are as defined above; and

A is

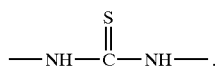

See Structure H.

Structure H

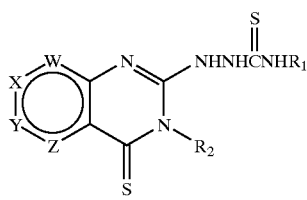

Another preferred class of compounds is that of Formula I wherein:

W, X, Y and Z are selected from C—$R_3$, C—$R_4$, C—$R_5$, C—$R_6$ and N and at least one and no more than two W, X, Y and Z are N;

$R_1$, $R_2$, $R_3$, $R_4$, $R_5$ and $R_6$ are as defined above;

M is oxygen; and

A is

See Structure I-A.

Structure I-A

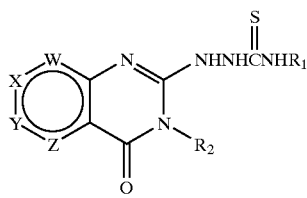

Another preferred class of compounds is that of Formula I-A wherein:

W, X, Y and Z are selected from C—$R_3$, C—$R_4$, C—$R_5$, and C—$R_6$ wherein $R_3$, $R_4$, $R_5$ and $R_6$ are as defined above except none can be hydrogen or halogen;

M is oxygen;

A is

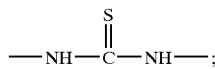

and $R_1$ and $R_2$ are as defined above. See Structure I-A above.

Another preferred class of compounds is that of Formula I-A wherein:

W, X, Y and Z are selected from C—$R_3$, C—$R_4$, C—$R_5$, C—$R_6$, wherein $R_3$, $R_4$, $R_5$ and $R_6$ are independently selected from hydrogen and halogen;

M is oxygen;
A is

$R_1$ is as defined above but it cannot be phenyl, benzyl, naphthyl or mono substituted phenyl wherein substitutions are halogen, methyl and methoxy; $R_2$ is as defined above but it cannot be phenyl, naphthyl, benzyl, or mono substituted phenyl wherein substitutions are halogen, methyl, butoxy, iso-butoxy, methoxy, or disubstituted phenyl, wherein substituions are methyl. See Structure I-A above.

Another preferred class of compounds is that of Formula II:

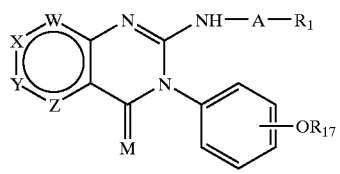

Formula II wherein W, X, Y and Z are each independently selected from C—$R_3$, C—$R_4$, C—$R_5$, C—$R_6$ and N (nitrogen) wherein no more than two of W, X, Y and Z are N;

M is oxygen or sulfur;
A is selected from the group consisting of:

(i) 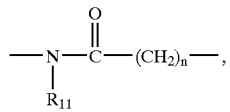

(ii) 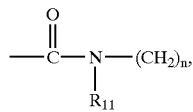

(iii) 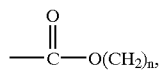

(iv) 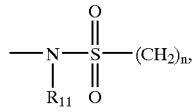

(v) 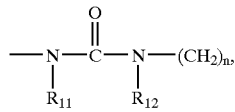

(vi) 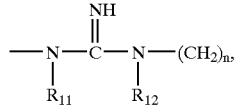

(vii) 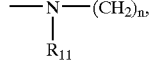

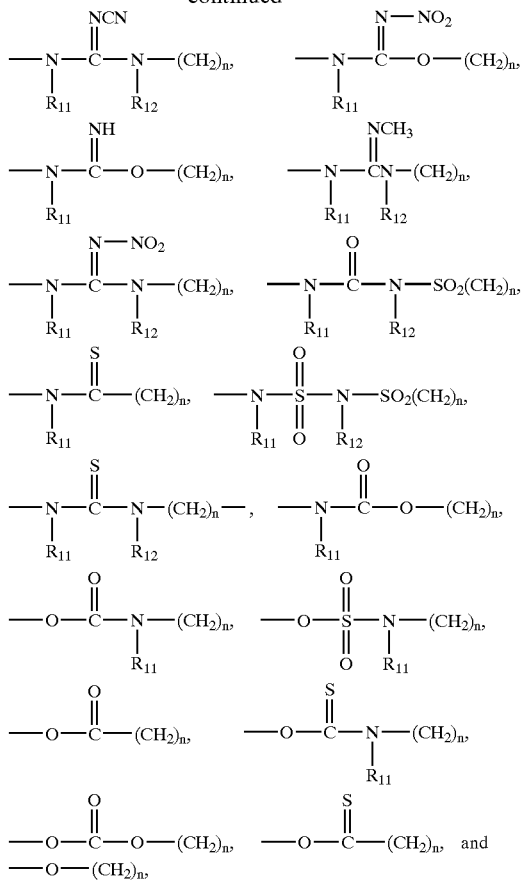

wherein $R_{11}$ and $R_{12}$ are independently hydrogen or lower alkyl (1–4 carbon atoms); n=0 or 1;

$R_1$, $R_3$, $R_4$, $R_5$, $R_6$, $R_7$, $R_8$, $R_{11}$, $R_{12}$, $R_{13}$, $R_{14}$, $R_{15}$, and $R_{16}$ are as defined in Formula I; and $R_{17}$ is an alkyl of 1 to 3 carbon atoms.

Another preferred class of compounds is that of Formula I wherein:

W, X, Y, and Z are each independently selected from C—$R_3$, C—$R_4$, C—$R_5$, C—$R_6$ and wherein $R_3$, $R_4$, $R_5$ and $R_6$ are independently selected from hydroxy, sulfhydryl, lower alkoxy, lower thioalkoxy, lower alkyl, CN, $CF_3$, $NO_2$, $COOR_7$, $NR_7R_8$, wherein $R_7$ and $R_8$ are as defined above;

M is oxygen; and
$R_1$ and $R_2$ are as defined above.

Another preferred class of compounds is that of Formula I wherein:

W, X, Y and Z are each independently selected from C—$R_3$, C—$R_4$, C—$R_5$, C—$R_6$ and wherein $R_3$, $R_4$, $R_5$ and $R_6$ are as defined above but they cannot be hydrogen or halogen;

M is oxygen;
A is

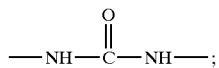

and
$R_1$ and $R_2$ are as defined above.

Another class of preferred compounds is that of Formula I wherein:

W, X, Y and Z are each independently selected from C—$R_3$, C—$R_4$, C—$R_5$, and C—$R_6$ wherein $R_3$, $R_4$, $R_5$ and $R_6$ are each independently hydrogen and halogen, A is

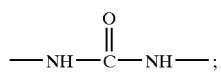

$R_1$ is as defined above but it cannot be phenyl, naphthyl or mono substituted phenyl wherein the substitution is chloro or bromo when $R_2$ is phenyl or mono substituted phenyl wherein substituion is chloro, bromo, n-butyl, n-butoxy, or iso-butoxy.

Another preferred class of compounds is that of Formula I wherein:

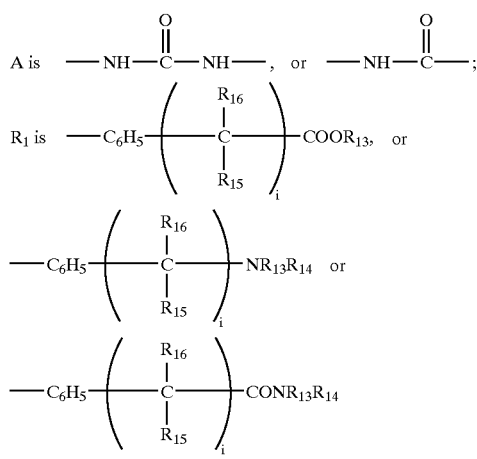

$R_{13}$ and $R_{14}$ are each independently selected from hydrogen, methyl, ethyl, and t-butyl;

wherein $R_{15}$, and $R_{16}$ are independently selected from hydrogen, methyl and ethyl;

i is 0 or 1;

M is O (oxygen); and

W, X, Y, Z and $R_2$ are as defined above.

The compounds as described herein may be prepared as follows.

Scheme I illustrates the process of making intermediates useful in preparation of desired compounds of the instant invention (Kottke et al., Pharmazie, 37, 635–637 (1982). Treatment of 1 with an appropriate isothiocyanate in refluxing acetic acid can give compound 2. Reaction of 2 with hydrazine in refluxing ethanol can give compound 3.

Scheme II illustrates the process of making compounds of present invention by acylation of intermediate Compound 3 by an appropriate acylating agent.

Compounds for which no preparation is given can be made by methods known in the literature or are of common knowledge by a skilled artisan.

The biological activity of compounds of the present invention may be evaluated by employing an initial screening test which rapidly and accurately measures the binding of the tested compound to known CCK receptor sites. Specific CCK receptors have been shown to exist in the central nervous system. (See Hays et al, *Neuropeptides* 1:53–62, 1980; and Satuer et al, *Science* 208:1155–1156, 1980).

In this screening test, the cerebral cortices taken from male CFLP mice weighing between 30–40 g were dissected on ice, weighed, and homogenized in 10 volumes of 50 mM Tris-HCl buffer (pH 7.4 at 0–4° C.). The resulting suspension was centrifuged, the supernate was discarded, and the pellet was washed by resuspension in Tris-HCl buffer followed by recentrifugation. The final pellet was resuspended in 20 volumes of 10 nM Hepes buffer (pH 7.2 at 23° C.) containing 130 mM NaCl, 4.7 nM KCl, 5 nM $MgCl_2$, 1 nM (0.25 mg/mL).

In saturation studies, cerebral cortical membranes were incubated at 23° C. for 120 minutes in a final volume of 500 μL of Hepes incubation buffer (pH 7.2) together with 0.2–20 nM tritiated—pentagastrin (Amersham International, England).

In the displacement experiments, membranes were incubated with a single concentration (2 nM) of ligand, together with increasing concentrations ($10^{11}$ to $10^{14}$ M) of competitive test compound. In each case, the nonspecific binding was defined as that persisting in the presence of the unlabeled octapeptide $CCK_{26-33}$ ($10^{-6}$M).

Following incubation, radioactivity bound to membranes was separated from that free in solution by rapid filtration through Whatman GF/B filters and washed three times with 4 mL of ice cold Tris-HCl buffer. Filters from samples incubated with tritiated-pentagastrin were placed in polyethylene vials with 4 mL of scintillation cocktail, and the radioactivity was estimated by liquid scintillation spectrometry (efficiency 47–52%).

The specific binding to CCK receptor sites was defined as the total bound tritiated-pentagastrin minus the amount of tritiated-pentagastrin bound in the presence of $10^{-6}$ octapeptide, $CCK_{26-33}$.

Saturation curves for specific tritiated-pentagastrin binding to mouse cortical membranes were analyzed by the methods of Scatchard (*Ann. New York Acad. Sci.* 51:660–672, 1949, and Hill (*J. Physiol.* 40:IV–VIII, 1910), to provide estimates for the maximum number of binding sites ($B_{max}$) and the equilibrium dissociation constant ($K_a$).

In displacement experiments, inhibition curves were analyzed by either logit-log plots or the iterative curve fitting computer program ALLFIT (DeLean, Munson and Redbard, 1978) to provide estimates of the $IC_{50}$ and nH (apparent Hill coefficient values). ($IC_{50}$ values were defined as the concentration of test compound required to produce 50% inhibition of specific binding).

The inhibition constant ($K_i$) of the test compound was then calculated according to the Cheng-Prusoff equation:

$$K_i = \frac{IC_{50}}{1 + [L]/K_a}$$

where [L] is the concentration of radiolabel and $K_a$ is the equilibrium dissociation constant.

The $K_i$ values for several representative compounds of the present invention are present in Table I.

The procedures described hereinbelow are useful for testing the utility of the compounds of the present invention as appetite suppressants.

In the Palatable Diet Feeding assay, adult male Hooded Lister rats weighing between 200–400 g are housed individually and trained to eat a palatable diet. This diet consists of Nestles sweetened condensed milk, powered rat foot and rat water which, when blended together, set to a firm consistency. Each rat is presented with 20–30 g of the palatable diet for 30 minutes per day during the light phase of the light-dark cycle over a training period of five days.

The intake of palatable diet is measured by weighing the food containing before and after the 30-minute access period (limits of accuracy 0.1 g). Care is taken to collect and correct for any spillage of the diet. Rats are given free access to pellet foot and water except during the 30-minute test period.

After the training period, dose-responsive curves are constructed for CCK8 and several representative compounds of the present invention (n=8–10 rats per dose level). $MPE_{50}$ values (±95% confidence limits) are obtained for the anorectic effects of these compounds.

In therapeutic use as appetite suppression agents, the compounds of the instant invention are administered to the patient at dosage levels of from about 200 to about 2800 mg per day.

Male Hooded Lister rats (175–250 g) are housed individually and are caused to fast overnight (free access to water). They are anesthetized with urethan (1.5 g/kg IP) and the trachea cannulated to aid spontaneous respiration. The stomach is perfused continuously using a modification of the original method of Ghosh & Schild in "Continuous Recording Of Acid Secretion In The Rat", *Brit. J. Pharmac.* 13:54–61, 1956 as described by Parsons in "Quantitative Studies of Drug-Induced Gastric Acid Secretion". (Ph.D. Thesis, University of London, 1969). The cavity of the stomach is perfused at a rate of 3 mL/min with 5.4% w/v glucose solution through both the esophageal and body cannula. The fluid is propelled by a roller pump (Gilson, Minipuls 2), through heating coils to bring its temperature to 37±1° C. The perfusion fluid is collected by the fundic collecting funnel and passed to a pH electrode connected to a Jenway pH meter (PHM6). An output is taken from the pH meter to a Rikadenki chart recorder for the on-line recording of the pH of the gastric perfusate.

Pentagastrin is stored as a frozen aliquot and diluted to the required concentrations with sterile 0.9% w/v NaCl. Novel compounds are dissolved in sterile 0.9% w/v NaCl on the day of the experiment. Drugs are administered IV through a cannulated jugular vein as a bolus in a dose volume of 1 mL/kg washed in with 0.15 mL 0.5% w/v NaCl. Basal pH is allowed to stabilize before administration of compounds is begun. Typically 30 minutes elapses between surgery and the first compound administration.

The compounds of the instant invention are also useful as antiulcer agents as discussed hereinbelow.

Aspirin-induced gastric damage is assessed in groups of 10 rats each.

All animals are made to fast for 24 hours before and during the experiment. Drug or vehicle is given 10 minutes before an oral dose of 1 mL of a 45-mg/ml suspension of aspirin in 0.5% carboxymethylcellulose (CMC).

The animals are sacrificed 5 hours after aspirin administration and the stomachs removed and opened for examination.

| Score | |
|---|---|
| 1 | Small hemorrhage |
| 2 | Large hemorrhage |
| 3 | Small ulcer |
| 4 | Large ulcer |
| 5 | Perforated ulcer |

The specific dosages may, however, be varied depending upon the patient, the severity of the condition being treated, and the activity of the compound employed. Determination of optimum dosages is within the skill of the art.

The compounds of the instant invention are also useful as anxiolytic agents as described and discussed below. Anxiolytic activity is assessed in the light/dark exploration test in the mouse (B. J. Jones, et al, *Brit. J. Pharmac.* 93:985–993, 1988).

The apparatus used is an open-topped box, 45 cm long, 27 cm wide, and 27 cm high, divided into a small (2/5) area and a large (3/5) area by a partition that extended 20 cm above the walls. There is a 7.5×7.5 cm opening in the partition at floor level. The small compartment is painted black and the large compartment white. The floor of each compartment is marked into 9 cm squares. The white compartment is illuminated by a 100-watt tungsten bulb 17 cm above the box and the black compartment by a similarly placed 60-watt red bulb. The laboratory is illuminated with red light.

All tests are performed between 13 hundred hours, 0 minutes and 18 hundred hours, 0 minutes. Each mouse is tested by placing it in the center of the white area and allowing it to explore the novel environment for five minutes. Its behavior is recorded on videotape and the behavioral analysis is performed subsequently from the recording. Five parameters are measured: the latency to entry into the dark compartment, the time spent in each area, the number of transitions between compartments, the number of lines crossed in each compartment, and the number of rears in each compartment.

In this test, an increase in the time spent in the light area is a sensitive measure of, that is directly related to, the anxiolytic effects of several standard anxiolytic drugs. Drugs were dissolved in water or saline and administered either subcutaneously, intraperitoneally, or by mouth (PO) via a stomach needle.

The compounds of the instant invention are useful as antipsychotic agents and can be tested for their ability to reduce the effects of intra-accumbens amphetamine in the rat as described hereinafter.

Male Sprague Dawley (CD) Bradford strain rats are used. The rats are housed in groups of five at a temperature of 21±2° C. on a 12 hour light-dark cycle of lights-on between 07 hours 00 minutes and 20 hours 00 minutes. Rats are fed CRM diet (Labsure) and allowed water ad libitum.

Rats are anesthetized with chloral hydrate (400 mg/kg SC) and placed in a Kopf stereotaxic frame. Chronically indwelling guide cannulae (constructed of stainless steel tubing 0.65 mm diameter held bilaterally in Parspex holders) are implanted using standard stereo-taxic techniques to terminate 3.5 mm above the center of the nucleus accumbens (Ant. 9.4, Vert. 0.0, Lat. 1.6) or 5.0 mm above the central nucleus of the amygdala (Ant. 5.8, Vert.—1.8, Lat. ±4.5) (atlas of De Groot, 1959). The guides are kept patent during a 14-day recovery period using stainless steel stylets, 0.3 mm diameter, which extended 0.5 mm beyond the guide tips.

Rats are manually restrained and the stylets removed. Intracerebral injection cannulae, 0.3 mm diameter, are inserted and drugs delivered in a volume of 0.5 µL over 5 seconds (a further 55 seconds was allowed for deposition) from Hamilton syringes attached via polythene tubing to the injection units. Animals are used on a single occasion only.

Behavioral experiments are conducted between 07 hours 30 minutes and 21 hours 30 minutes in a quiet room maintained at 22±2° C. Rats are taken from the holding room and allowed 1 hour to adapt to the new environment. Locomotor activity 19 assessed in individual screened Perspex cages (25×15×15 cm (high)) (banked in groups of 30) each fitted with one photocell unit along the longer axis 3.5 cm from the side; this position has been found to minimize spurious activity counts due to, for example, preening and head movements when the animal is stationary. Interruptions of the light beam are recorded every 5 minutes. At this time animals are also observed for the presence of any nonspecific change in locomotor activity, e.g., sedation, prostration, stereotyped movements, that could interfere with the recording of locomotor activity.

The abilities of the compounds of the invention to inhibit the hyperactivity are tested as described hereinbelow.

An increase in locomotor activity followed the bilateral injection of amphetamine (20 μg) into the nucleus accumbens; peak hyperactivity (50 to 60 counts 5 minutes$^{-1}$) occurs 20 to 40 minutes after injection. This test is known to be predictive of antipsychotic activity (Costall, Domeney & Naylor & Tyers, Brit. J. Pharmac. 92:881–894).

The compounds of the instant invention prevent and treat the withdrawal response produced when chronic treatment by a drug is stopped or when alcohol abuse is stopped. These compounds are therefore expected to be useful as therapeutic agents in the treatment of chronic drug or alcohol abuse as discussed and described below.

The effect of the compounds of the instant invention is illustrated, for example, in the mouse "light/dark box" test wherein five animals are given nicotine, in a range of 0.1 to 100 mg/kg i.p. b.d. for 14 days. After a 24-hour withdrawal period, a compound of the invention is given at 1.0 mg/kg i.p. b.d. The increased time spent in the light area is a sensitive measure of the effect of a compound of the invention described herein as an agent to treat withdrawal effects from nicotine.

For preparing pharmaceutical compositions from the compounds of this invention, inert, pharmaceutically acceptable carriers can be used which are either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

The powders and tablets preferably contain 5% to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Pharmaceutically acceptable salts are acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydrochloride, hydroxynaphthoate, iodide, isethionate, lactate, lactobionate, malate, maleate, mandelate megylate, methylbromide, methylnitrate, methylsulfate, mucate, napsylate, nitrate, pamoate (embonate), pantothenate, phosphate/diphosphate, polygalacturonate, salicylate, stearate, subacetate, guccinate, sulfate, tannata, tartrate, teoclate, triethiodide, benzathine, chloroprocaine, choline, diethanolamine, ethylenediamine, meglumine, procaine, aluminum, calcium, lithium, magnegium, potassium, sodium, and zinc.

The term "preparation" is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form preparations include solutions, suspensions, and emulsions. Sterile water or water-propylene glycol solutions of the active compounds may be mentioned ag an example of liquid preparations suitable for parenteral administration. Liquid preparations can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

EXAMPLE A 3-(3-Isopropoxy-phenyl)-2-thioxo-2,3-dhydr-1H-quinazolin-4-one

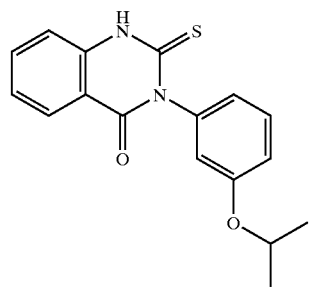

To a solution of 3-isopropoxy aniline (6.0 g, 40 mmol) in 150 ml of CHCl$_3$ was added dropwise thiophos-gene (2.81 ml, 44 mmol) at 0° C. After the addition of thiophosgene, triethylamine (7.0 ml, 48 mmol) was added slowly and the reaction mixture was stirred for 2 hours at room temperature. It was then concentrated and diluted with 200 ml of ethyl acetate. The triethylamine hydrochloride salt was filtered off and the filtrate was concentrated to yield crude 3-isopropoxyphenyl isothiocyanate.

The crude 3-isopropoxyphenyl isothiocyanate was dissolved in 150 ml of acetic acid, and anthranilic acid (6.04 g, 44 mmol) was added. The resulting reaction mixture was refluxed for 16 hours and then cooled to room temperature. The white solid was separated which was filtered to yield 9.0 g of the title compound (72.1%) mp 288–290° C.

In a process analogous to Example A using appropriate starting materials, the corresponding compounds are prepared as follows:
2-Thioxo-3-o-tolyl-2,3-dihydro-1H-quinazolin-4-one
3-(2-Ethyl-phenyl)-2-thioxo-2,3-dihydro-1H-quinazolin-4-one
3-(4-Chloro-phenyl)-2-thioxo-2,3-dihydro-1H-quinazolin-4-one
3-(2,3-Dichloro-phenyl)-2-thioxo-2,3-dihydro-1H-quinazolin-4-one
3-(3-Fluoro-phenyl)-2-thioxo-2,3-dihydro-1H-quinazolin-4-one
3-Naphthalen-1-yl-2-thioxo-2,3-dihydro-1H-quinazolin-4-one
3-(3-Methoxy-phenyl)-2-thioxo-2,3-dihydro-1H-quinazolin-4-one
2-Hydrazino-3-(3-methoxy-phenyl)-3H-quinazolin-4-one
3-(3-Dimethylamino-phenyl)-2-thioxo-2,3-dihydro-1H-quinazolin-4-one
3-[4-(Morpholine-4-sulfonyl)-phenyl]-2-thioxo-2,3-dihydro-1H-quinazolin-4-one
3-Pyridin-3-yl-2-thioxo-2,3-dihydro-1H-quinazolin-4-one
3-(4-Methoxy-phenyl)-2-thioxo-2,3-dihydro-1H-quinazolin-4-one
3-(3-Nitro-phenyl)-2-thioxo-2,3-dihydro-1H-quinazolin-4-one
3-(3-Isopropoxy-phenyl)-2-thioxo-2,3-dihydro-1H-pyrido[2,3-d]pyrimidin-4-one
3-(3,4-Dimethoxy-phenyl)-2-thioxo-2,3-dihydro-1H-quinazolin-4-one

EXAMPLE A-1

3-(3-Amino-phenyl)-2-thioxo-2,3-dihydro-1H-quinazoln-4-one

A solution of 3-(3-Nitro-phenyl)-2-thioxo-2,3-dihydro-1H-quinazolin-4-one (4.8 g, 12.0 mmol) in 200 ml THF (tetrahydrofuran) was treated with Raney Ni (4.0 gm), and resulting suspension was subjected to atmosphere of hydrogen at 50.2 psi for 19 hours with agitation at temperature of 25° C. The mixture was then filtered through celite, and the solvent was removed in vacuo to give the title compound as a yellow solid. This crude product was then titurated with ethyl acetate and hexane to isolate product as a light yellow solid.

EXAMPLE B

2-Hydrazino-3-(3-isoprpoxy-phenyl)-3H-quinazolin-4-one

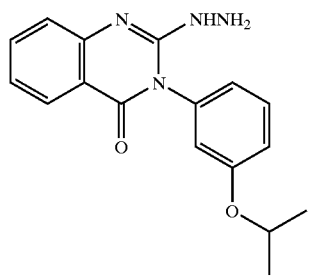

A mixture of 3-(3-isopropoxy-phenyl)-2-thioxo-2,3-dihydro-1H-quinazolin-4-one (Example-1) (3.12 g, 10 mmol) and anhydrous hydrazine (3.2 g, 100 mmol) in 100 ml of ethanol was refluxed for 18 hours. The reaction mixture was then cooled and white solid was separated which was filtered to obtain 1.2 g (38%) of title compound as white solid. The filtrate was concentrated and an additional 1.6 g (50.4%) of title compound was isolated by crystallization from ethyl acetate. mp 158–160° C.

In a process analogous to Example B using appropriate starting materials, the corresponding compounds are prepared as follows:
2-Hydrazino-3-o-tolyl-3H-quinazolin-4-one
3-(2-Ethyl-phenyl)-2-hydrazino-3H-quinazolin-4-one
3-(4-Chloro-phenyl)-2-hydrazino-3H-quinazolin-4-one
3-(2,3-Dichloro-phenyl)-2-hydrazino-3H-quinazolin-4-one
3-(3-Fluoro-phenyl)-2-hydrazino-3H-quinazolin-4-one
2-Hydrazino-3-naphthalen-1-yl-3H-quinazolin-4-one
2-Hydrazino-3-(3-methoxy-phenyl)-3H-quinazolin-4-one
3-(3-Fluoro-phenyl)-2-hydrazino-3H-quinazolin-4-one
3-(3-Dimethylamino-phenyl)-2-hydrazino-3H-quinazolin-4-one
2-Hydrazino-3-[4-(morpholine-4-sulfonyl)-phenyl]-3H-quinazolin-4-one
2-Hydrazino-3-pyridin-3-yl-3H-quinazolin-4-one
2-Hydrazino-3-(4-methoxy-phenyl)-3H-quinazolin-4-one
3-(3-Amino-phenyl)-2-hydrazino-3H-quinazolin-4-one
2-Hydrazino-3-(3-isopropoxy-phenyl)-3H-pyrido[2,3-d]pyrimidin-4-one
3-(3,4-Dimethoxy-phenyl)-2-hydrazino-3H-quinazolin-4-one

EXAMPLE-1

Hydrazinecarboxamide, N-(4-bromophenyl)-2-[3,4-dihydro-3-[3-(1-methylethoxy)-phenyl]-4-oxo-2-quinazolinyl]-

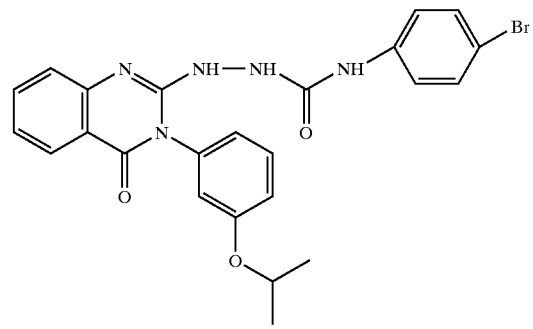

2-Hydrazino-3-(3-isopropoxy-phenyl)-3H-quinazolin-4-one (0.155 g, 0.5 mmol) was dissolved in 5.0 ml CH$_3$CN and 4-bromophenyl isocyanate (0.1 g, 0.5 mmol) was added at room temperature. The resulting reaction mixture was stirred at room temperature for 16 hours. The white solid was separated which was filtered and washed with CH$_3$CN. The title compound was obtained as white solid (0.12 g, 47.2%) mp. 212° C.

C$_{24}$H$_{22}$Br$_1$N$_5$O$_3$

|  | C | H | N |
|---|---|---|---|
| Calc: | 56.70 | 4.36 | 13.78 |
| Found: | 56.59 | 4.38 | 13.58 |

EXAMPLE-2

Benzoic Acid, 3-[[[2-[3,4-dihydro-[3-(1-methylethoxy)phenyl]-4-oxo-2-quinazolinyl-hydrazino]carbonyl]amino]-ethyl Ester

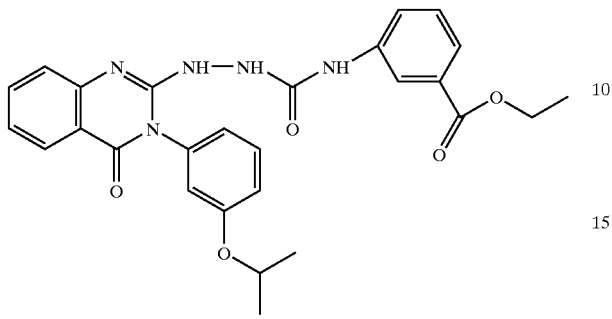

The title compound was prepared by the method as described for Example 1, but using 3-ethyoxycarbonylphenyl isocyanate. The title compound was isolated as a white solid (0.32 g, 62%) mp 190–191° C.
$C_{27}H_{27}N_5O_3$

|  | C | H | N |
|---|---|---|---|
| Calc: | 64.66 | 5.43 | 13.96 |
| Found: | 64.42 | 5.33 | 13.93 |

EXAMPLE-3

Hydrazinecarboxamide, 2-[3,4-dihydro-3-[3-(1-methylethoxy)phenyl-4-oxo-2-quinazolinyl]-N-(4-methoxyphenyl)-

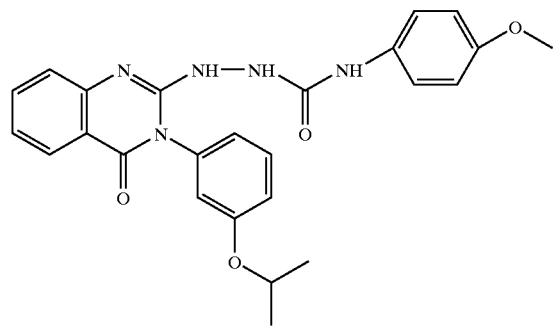

The title compound was prepared by the method as described for Example 7, but using 4-methoxyphenyl isocyanate. The title compound was isolated as a white solid (0.13 g, 56.6%) mp 194–195° C.
$C_{25}H_{25}N_5O_4$

|  | C | H | N |
|---|---|---|---|
| Calc: | 65.35 | 5.48 | 15.24 |
| Found: | 65.18 | 5.28 | 15.32 |

EXAMPLE-4

Hydrazinecarboxamide, 2-[3,4-dihydro-3-[3-(1-methylethoxy)phenyl]-4-oxo-2-quinazoliny]-N-(3-methoxyphenyl)-

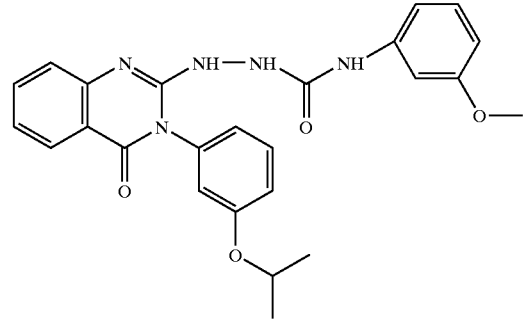

The title compound was prepared by the method as described in Example-7, but using 3-methoxyphenyl isocyanate. The title compound was isolated as a white solid (0.1 g, 5.2%) mp 204–205° C.
$C_{25}H_{25}N_5O_4$

|  | C | H | N |
|---|---|---|---|
| Calc: | 65.35 | 5.48 | 15.24 |
| Found: | 65.12 | 5.43 | 15.63 |

EXAMPLE-5

Hydrazinecarboxamide, 2-[3,4-dihydro-3-[3-(1-methylethoxy)phenyl]-4-oxo-2-quinazolinyl]-N-(2-methoxyphenyl)-

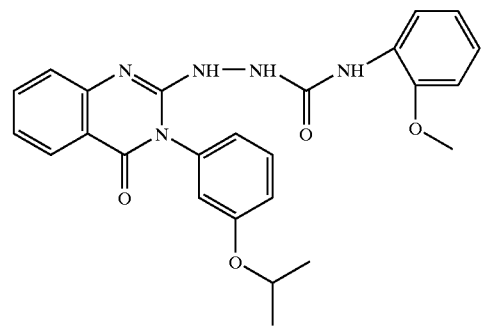

The title compound was prepared by the method as described in Example-7, but using 2-methoxyphenyl isocyanate. The title compound was isolated as a white solid (0.17 g, 74%) mp 209–211° C.
$C_{25}H_{25}N_5O_4$

|  | C | H | N |
|---|---|---|---|
| Calc: | 65.35 | 5.48 | 15.24 |
| Found: | 65.18 | 5.28 | 15.32 |

EXAMPLE-6

Hydrazinecarboxamide, 2-[3,4-dihydro-3-[3-(1-methylethloxy)phenyl]-4-oxo-2-quinazolinyl-N-[(4-trifluoromethyl)phenyl]-

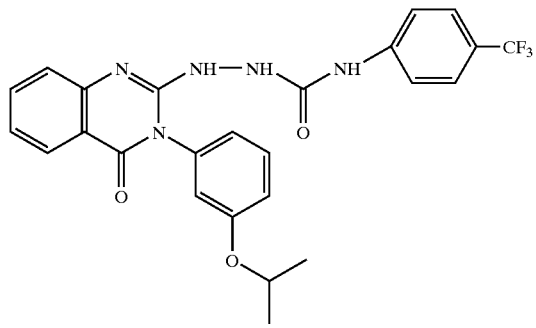

The title compound was prepared by the method as described in Example-7, but using α, α, α-trifluorotoyl isocyanate. The title compound was isolated as a white solid (0.13 g, 52.3%) mp 201–202° C.
$C_{25}H_{22}F_3N_5O_3$

|  | C | H | N |
|---|---|---|---|
| Calc: | 60.36 | 4.46 | 14.08 |
| Found: | 60.18 | 4.52 | 14.03 |

EXAMPLE-7

Benzoic Acid, 3-[[[2-[3,4-dihydro-[3-[(1-methylethoxy)phenyl]-4-oxo-2-quinazolinyl]-hydrazrino]carbonyl]amino]-, 1,1-dimethylethyl Ester

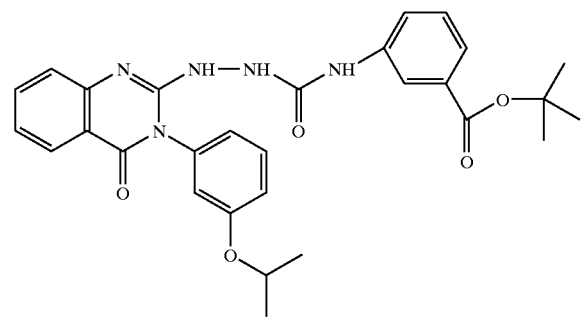

The title compound was prepared by the method as described in Example-7, but using 3-tert-butoxycarbonyl-phenyl isocyanate. The title compound was isolated as a white solid (0.15 g, 56.7%) mp 185–186° C.
$C_{29}H_{31}N_5O_5$

|  | C | H | N |
|---|---|---|---|
| Calc: | 65.77 | 5.90 | 13.22 |
| Found: | 65.78 | 6.06 | 13.03 |

EXAMPLE-8

Hydrazinecarboxamide, 2-[3,4-dihydro-3-[3-(1-methylethoxy)phenyl]-4-oxo-2-quinazolinyl-N-(3-methylphenyl)-

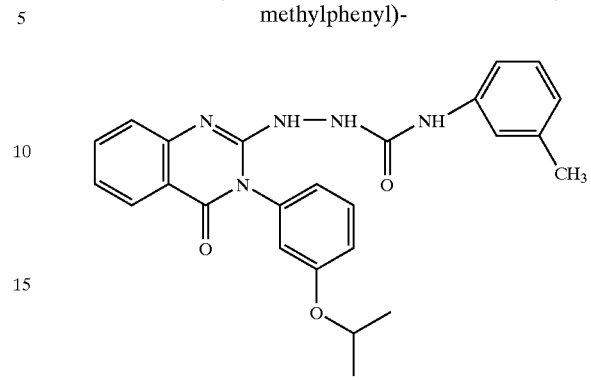

The title compound was prepared by the method as described in Example-7, but using 3-tolyl isocyanate. The title compound was isolated as a white solid (0.16 g, 72%) mp 204° C.
$C_{25}H_{25}N_5O_3$

|  | C | H | N |
|---|---|---|---|
| Calc: | 67.71 | 5.68 | 15.79 |
| Found: | 67.75 | 5.28 | 15.80 |

EXAMPLE-9

Hydrazinecarboxamide, N-(3,5-dichoro-4-pyridinyl)-2-[3,4-dihydro-3-[3-(1-methyl-ethoxyy)phenyl(4-oxo-2-quinazolinyl

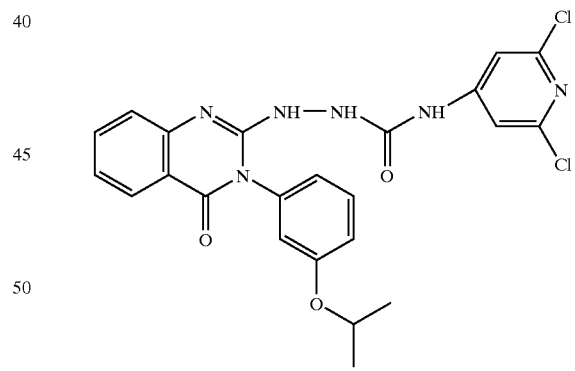

The title compound was prepared by the method as described in Example-7, but using 2,6-dichloropyridyl-4-isocyanate. The title compound was isolated as a white solid (0.32 g, 64.1 μ%) mp 225° C.
$C_{23}H_{20}Cl_2N_6O_3$

|  | C | H | Cl | N |
|---|---|---|---|---|
| Calc: | 55.32 | 4.04 | 14.20 | 16.83 |
| Found: | 55.12 | 4.04 | 14.26 | 16.80 |

EXAMPLE-10

Benzoic Acid, 4-[[[2-[3,4-dihydro-3-[3-(1-methylethoxy)phenyl]-4-oxo-2-quinazolinyl]-hydrazino]carbonyl]amino]-ethyl Ester

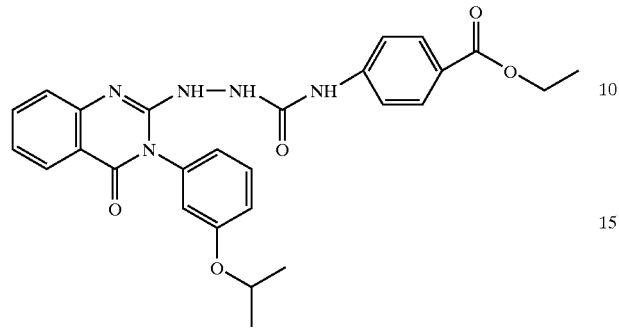

The title compound was prepared by the method as described for Example-7, but using 4-ethoxycarbonylphenyl isocyanate. The title compound was isolated as a white solid (0.28 g, 55.8%) mp 190–191° C.
$C_{27}H_{27}N_5O_5$

|  | C | H | N |
|---|---|---|---|
| Calc: | 64.66 | 5.43 | 13.96 |
| Found: | 64.47 | 5.35 | 13.99 |

EXAMPLE-11

Benzoic Acid, 2-[[[2-[3,4-dihydro-3-[3-(1-methylethoxy)phenyl]-4-oxo-2-quinazolinyl]-hydrazino]carbonyl]amino]-, ethyl Ester

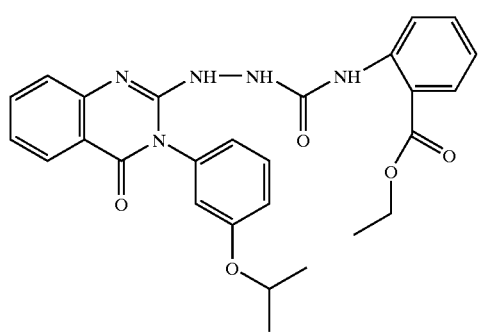

The title compound was prepared by the method as described for Example-7, but using 3-ethoxycarbonylphenyl isocyanate. The title compound was isolated as a white solid (0.32 g, 62%) mp 194–195° C.
$C_{27}H_{27}N_5O_5$ 0.32 $C_4H_8O_2$

|  | C | H | N |
|---|---|---|---|
| Calc: | 64.12 | 5.62 | 13.22 |
| Found: | 63.75 | 5.41 | 13.44 |

EXAMPLE-12

Benzoic Acid, 3-[[[2-[3,4-dihydro-3-[3-(1-methylethoxy)phenyl]-4-oxo-2-quinazolinyl]-hydrazino]carbonyl]amino]-

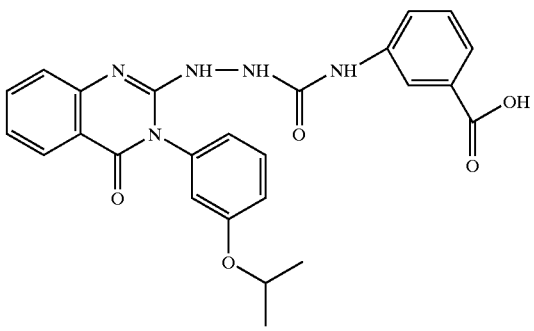

Benzoic acid, 3-[[(2-[3,4-dihydro-3-[3-(1-methylethoxy)-phenyl]-4-oxo-2-quinazolinyl]hydrazino]carbonyl]amino]-1,1-dimethylethyl ester (0.317 g, 0.6 mmol) in 10 ml of formic acid was stirred overnight at room temperature. The reaction mixture was concentrated, diluted with toluene and again concentrated. The residue was diluted with ethyl acetate. The white solid was separated which was filtered to yield 0.25 g (88%) of title compuond as a white solid. mp 207° C.
$C_{27}H_{23}N_5O_5 \cdot 0.28\ H_2O$

|  | C | H | N |
|---|---|---|---|
| Calc: | 62.75 | 4.96 | 14.63 |
| Found: | 62.65 | 4.93 | 14.65 |

EXAMPLE 13

Hydrazinecarboxamide, N-(4-Chlorophenyl)-2-[3,4-dihydro-3-[3-(1-methylethoxy)phenyl]-4-oxo-2-quinazolinyl]

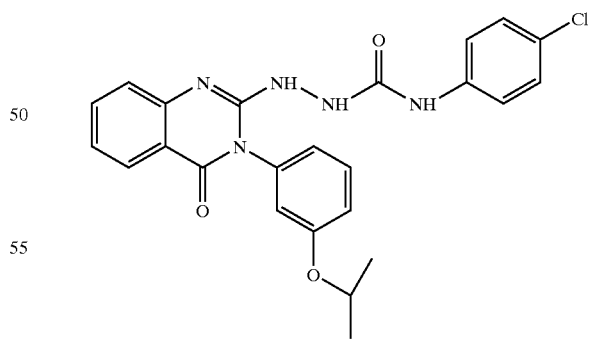

The titled compound was prepared by the method as described for Example 1, but using 4-chlorophenyl isocyanate. The title compound was isolated as a white solid (0.16 g, 69%) mp 204–206° C.
$C_{24}H_{22}ClN_5O_3$
Calc.: C, 62.14; H, 4.78; N, 15.10
Found: C, 61.85; H, 4.66; N, 15.35

EXAMPLE 14

Hydrazinecarboxamide, N-(3-cyanohenyl)-2-[3,4-dihydro-3-[3-(1-methylethoxoy)phenyl]-4-oxo-2-quinazolinyl]-

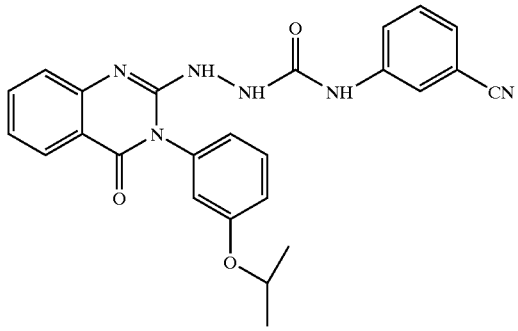

The titled compound was prepared by the method as described for Example 1, but using 3-cyanophenyl isocyanate. The title compound was isolated as a white solid (1.1 g, 80%) mp 195° C.

$C_{25}H_{22}N_6O_3$
Calc.: C, 66.07; H, 4.88; N, 18.49
Found: C, 65.97; H, 4.92; N, 18.88

EXAMPLE 15

Hydrazinecarboxamide, N-(cyclohexyl)-2-[3,4-dihydro-3-[3-(1-methylethoxy)phenyl]-4-oxo-2-quinazolinyl]-

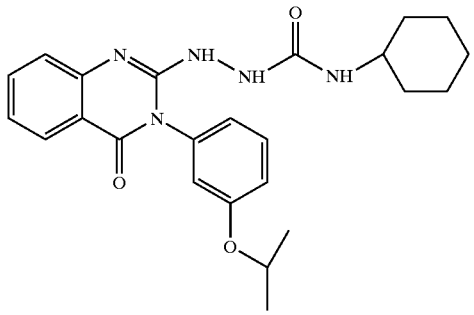

The titled compound was prepared by the method as described for Example 1, but using cyclohexyl isocyanate. The title compound was isolated as a white solid (0.2 g, 92%) mp 205–207° C.

$C_{24}H_{29}N_5O_3$
Calc: C, 66.50; H, 6.28; N, 16.15
Found: C, 66.04; H, 6.68; N, 16.19

EXAMPLE 16

Benzoic Acid, 3-[[[2-[3,4-dihydro-3-(2-methylphenyl)-4-oxo-2-quinazolinyl]hydrazino]carbonyl]amino]-, Ethyl Ester

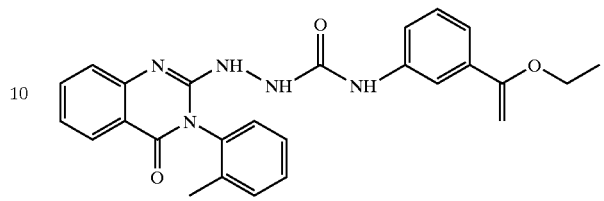

The titled compound was prepared by the method as described for Example 2, but using 2-hydrazino-3-O-tolyl-3H-quinazolin-4-one. The title compound was isolated as a white solid (0.5 g, 54.6%) mp 206–207° C.

$C_{25}H_{23}N_5O_4$
Calc.: C, 65.64; H, 5.03; N, 15.36
Found: C, 65.64; H, 5.07; N, 15.31

EXAMPLE 17

Benzoic Acid, 3-[[[2-[3-(2-ethylphenyl)-3,4-dihydro-4-oxo-2-quinazolinyl]hydrazino]carbonyl]amino]-, Ethyl Ester

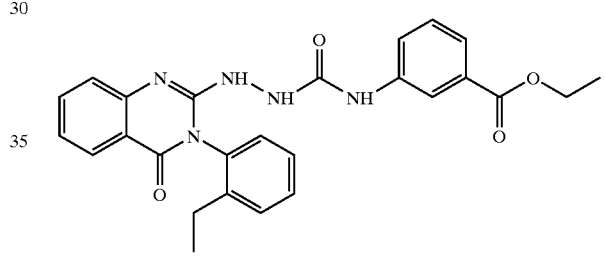

The titled compound was prepared by the method as described for Example 2, but using 3-(2-ethylphenyl)-2-hydrazino-3H-quinazolin-4-one. The title compound was isolated as a white solid (0.76 g, 79.7%) mp 196° C.

$C_{26}H_{25}N_5O_4$
Calc.: C, 66.06; H, 5.32; N, 14.80
Found: C, 66.23; H, 5.34; N, 14.85

EXAMPLE 18

Benzoic acid, 3-[[[2-[3-(4-chlorophenyl)-3,4-dihydro-4-oxo-2-quinazolinyl]hydrazino]carbonyl]amino]-, Ethyl Ester

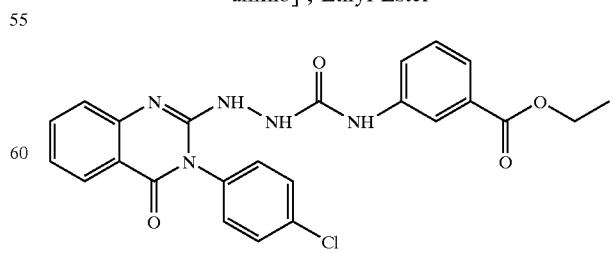

The titled compound was prepared by the method as described for Example 2, but using 3-(4-chlorophenyl)-2- hydrazino-3H-quinazolin-4-one. The title compound was isolated as a white solid (0.82 g, 80%) mp 228–229° C.

$C_{24}H_{20}Cl_1N_5O_4$
Calc.: C, 60.32; H, 4.22; N, 14.65; Cl, 7.42
Found: C, 60.13; H, 3.79; N, 14.61; Cl, 7.73

EXAMPLE 19

Benzoic Acid, 3-[[[2-[3-(3,4-dichlorophenyl)-3,4-dihydro-4-oxo-2-quinazolinyl]hydrazino]carbonyl]amino]-, Ethyl Ester

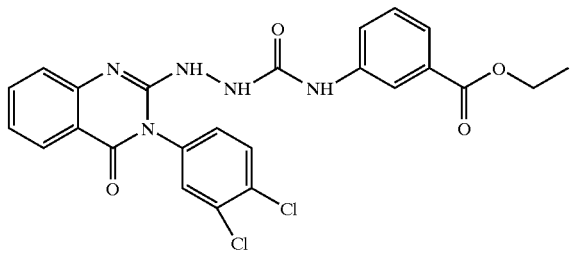

The titled compound was prepared by the method as described for Example 2, but using 3-(3,4-dichlorophenyl)-2-hydrazino-3H-quinazolin-4-one. The title compound was isolated as a white solid (0.82 g, 80%) mp 228–229° C.

$C_{24}H_{19}Cl_2N_5O_4$
Calc.: C, 56.26; H, 3.74; N, 13.67; Cl, 13.84
Found: C, 56.03; H, 3.35; N, 13.55; Cl, 13.67

EXAMPLE 20

Benzoic Acid, 3-[[[2-[3-(3-fluorophenyl)-3,4-dihydro-4-oxo-2-quinazolinyl]hydrazino]carbonyl]amino]-, Ethyl Ester

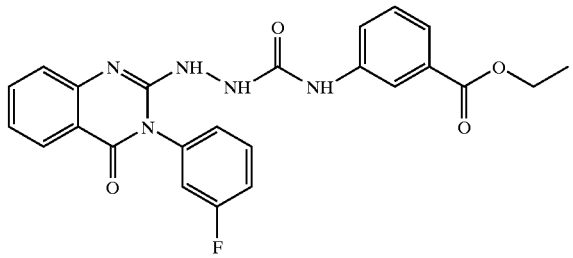

The titled compound was prepared by the method as described for Example 2, but using 3-(3-fluorophenyl)-2-hydrazino-3H-quinazolin-4-one. The title compound was isolated as a white solid (0.75 g, 81.26%) mp 217–218° C.

$C_{24}H_{20}F_1N_5O_4$
Calc.: C, 62.47; H, 4.37; N, 15.18; F, 4.12
Found: C, 62.15; H, 4.02; N, 15.12; F, 4.10

EXAMPLE 21

Benzoic Acid, 3-[[[2-(3,4-dihydro-1-naphthalenyl-2-quinazolinyl)hydrazino]carbonyl]amino]-, Ethyl Ester

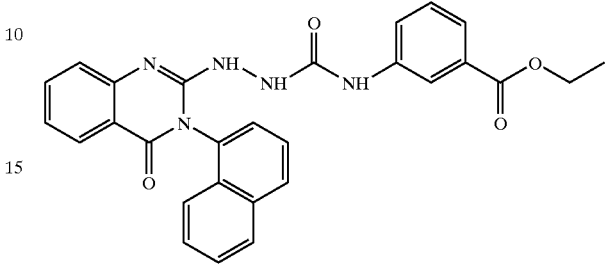

The titled compound was prepared by the method as described for Example 2, but using 2-hydrazino-1-naphthalen-3-yl-3H-quinazolin-4-one. The title compound was isolated as a white solid (0.9 g, 93%) mp 258–259° C.

$C_{28}H_{23}N_5O_4 \cdot 0.38H_2O_1$
Calc.: C, 67.21; H, 4.79; N, 14.00
Found: C, 67.21; H, 4.79; N, 14.01

EXAMPLE 22

Benzoic Acid, 3-[[[2-[3,4-dihydro-3-(3-methoxyphenyl)-4-oxo-2-quinazolinyl]hydrazino]carbonyl]amino]-, Ethyl Ester

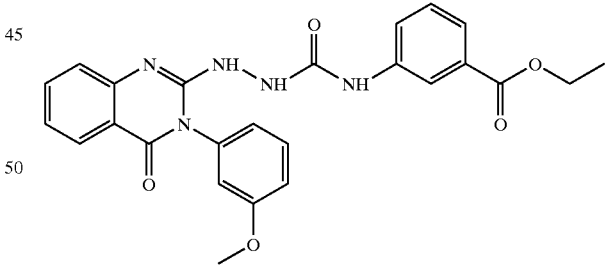

The titled compound was prepared by the method as described for Example 2, but using 2-hydrazino-3-(3-methoxyphenyl)-3H-quinazolin-4-one. The title compound was isolated as a white solid (0.34 g, 71.8%) mp 195–196° C.

$C_{25}H_{23}N_5O_4$
Calc.: C, 63.42; H, 4.90; N, 14.79
Found: C, 63.20; H, 4.85; N, 14.84

EXAMPLE 23

Benzoic Acid, 3-[[[2-[3-(3-chlorophenyl)-3,4-oxo-2-quinazolinyl]hydrazino]carbonyl]amino]-, Ethyl Ester

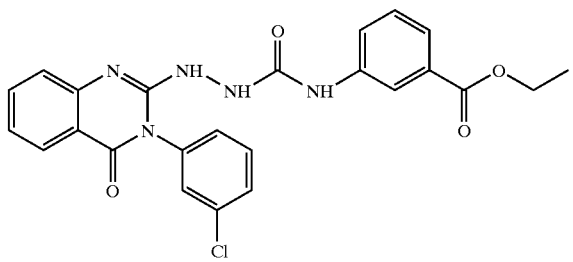

The titled compound was prepared by the method as described for Example 2, but using 3-(3-chlorophenyl)-2-hydrazino-3H-quinazolin-4-one. The title compound was isolated as a white solid (0.11 g, 23%) mp 214–215° C.

$C_{24}H_{20}Cl_1N_5O_4$
Calc.: C, 60.32; H, 4.22; N, 14.65
Found: C, 60.29; H, 4.41; N, 15.02

EXAMPLE 24

Benzoic Acid, 3-[[[2-[3-[3-(dimethylamino)phenyl]-3,4-dihydro-4-oxo-2-quinazolinyl]hydrazino]carbonyl]amino]-, Ethyl Ester

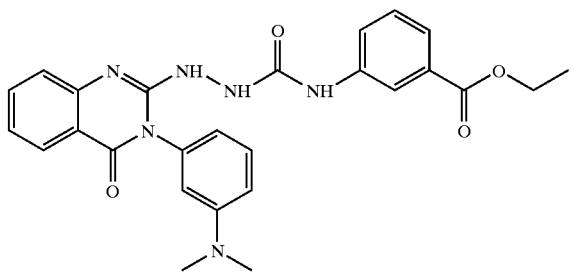

The titled compound was prepared by the method as described for Example 2, but using 3-[3-(dimethylamino)-phenyl]-2-hydrazino-3H-quinazolin-4-one. The title compound was isolated as a white solid (0.31 g, 60%) mp 207–209° C.

$C_{26}H_{26}N_6O_4$: 0.34 $C_4H_8O_2$
Calc.: C, 63.63; H, 5.60; N, 16.27
Found: C, 63.85; H, 5.80; N, 16.21

EXAMPLE 25

Benzoic Acid, 3-[[[2-[3,4-dihydro-3-[4-(4-morpholinyl-sulfonyl)phenyl]-4-oxo-2-quinazolinyl]hydrazino]carbony-1]amino]-, Ethyl Ester

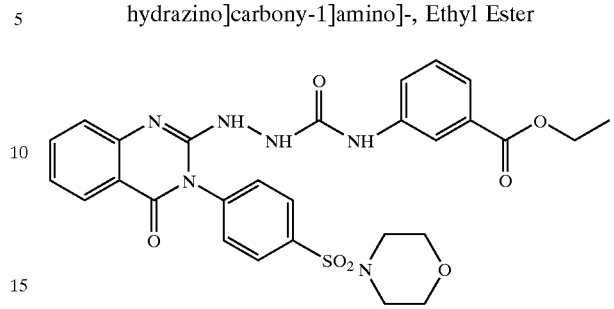

The titled compound was prepared by the method as described for Example 2, but using 2-hydrazino-3-[4-(4-morpholinylsulfonyl)phenyl]-3H-quinazolin-4-one. The title compound was isolated as a white solid (0.3 g, 50.6%) mp 180–184° C.
$C_{28}H_{28}N_6O_7S_1$
Calc.: C, 56.75; H, 4.76; N, 14.18
Found. C, 56.96; H, 5.10; N, 14.64

EXAMPLE 26

Benzoic Acid, 3-[[[2-[(3,4-dihydro-4-oxo-3-(3-pyridinyl)-2-quinoxalinYl]hydrazino]carbonyl]amino]-, Ethyl Ester

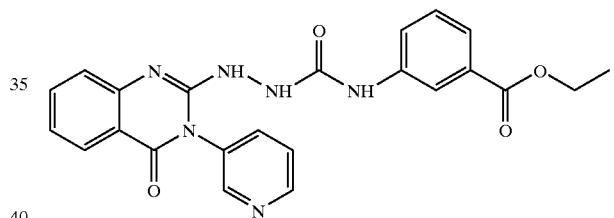

The titled compound was prepared by the method as described for Example 2, but using 2-hydrazino-3-pyridin-3-yl-3H quinazolin-4-one. The title compound was isolated as a white solid (0.3 g, 50.6%) mp 180–184° C.
$C_{23}H_{20}N_6O_4$
Calc.: C, 62.16; H, 4.54; N, 18.91
Found: C, 61.91; H, 4.58; N, 19.05

EXAMPLE 27

Hydrazinecarboxamide, 2-[3,4-dihydro-3-(2-methylphenyl)-4-oxo-2-quinazolinyl]-N-(3-methylphenyl)-

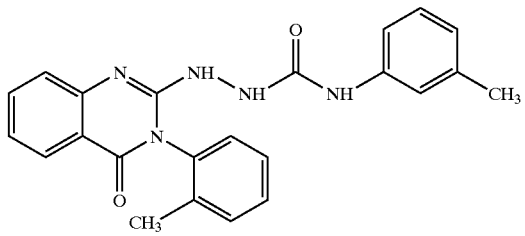

The titled compound was prepared by the method as described for Example 8, but using 2-hydrazino-3-o-tolyl- 3H-quinazolin-4-one. The title compound was isolated as a white solid (0.72 g, 90%) mp 180–183° C.

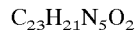
Calc.: C, 69.16; H, 5.30; N, 17.53
Found: C, 69.14; H, 5.45; N, 17.48

EXAMPLE 28

Hydrazinecarboxamide, 2-[3-(2-ethylphenyl)-3,4-dihydro-4-dihydro-4-oxo-2-quinazolinyl]-N-(3-methylphenyl)-

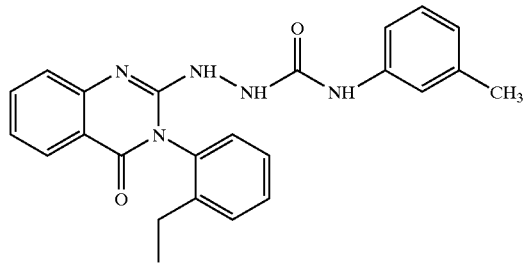

The titled compound was prepared by the method as described for Example 8, but using 3—(2-ethylphenyl)-2-hydrazino-3H-quinazolin-4-one. The title compound was isolated as a white solid (0.72 g, 90%) mp 180–183° C.

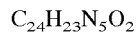
Calc.: C, 69.72; H, 5.61; N, 16.94
Found: C, 69.64; H, 5.57; N, 17.05

EXAMPLE 29

Hydrazinecarboxamide, 2-[3-(4-chlorophenyl)-3,4-dihydro-4-oxo-2-quinazolinyl]-N-(3-methylphenyl)-

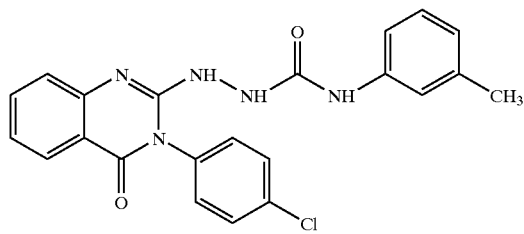

The titled compound was prepared by the method as described for Example 7, but using 3-(4-chlorophenyl)-2-hydrazino-3H-quinazolin-4-one. The title compound was isolated as a white solid (0.53 g, 63.3%) mp>320° C.

Calc.: C, 62.93; H, 4.32; N, 16.68
Found: C, 62.52; H, 4.15; N, 16.81

EXAMPLE 30

Hydrazinecarboxamide, 2-[3-(3,4-dichlorophenyl)-3,4-dihydro-4-oxo-2-quinazolinyl]-N-(3-methylphenyl)-

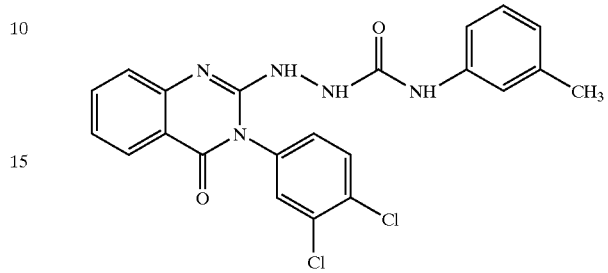

The titled compound was prepared by the method as described for Example 8, but using 3-(3,4-dichlorophenyl)-2-hydrazino-3H-quinazolin-4-one. The title compound was isolated as a white solid (0.75 g, 82.7%) mp 217° C.

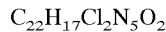
Calc.: C, 58.16; H, 3.77; N, 15.42
Found: C, 57.92; H, 3.61; N, 15.51

EXAMPLE 31

Hydrazinecarboxamide, 2-[3-(3-fluorophenyl)-3,4-dihydro-4-oxo-2-quinazolinyl]-N-(3-methylphenyl)-

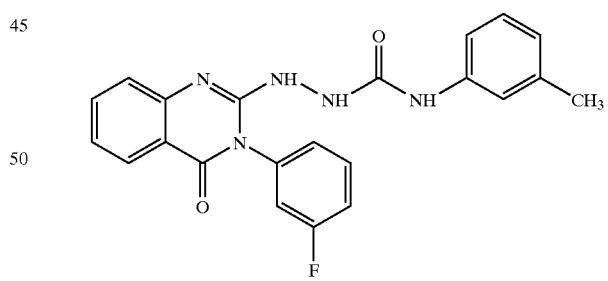

The titled compound was prepared by the method as described for Example 8, but using 3-(3-fluorophenyl)-2-hydrazino-3H-quinazolin-4-one. The title compound was isolated as a white solid (0.74 g, 91.7%) mp>320° C.

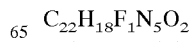
Calc.: C, 65.50; H, 4.50; N, 17.36
Found: C, 65.34; H, 4.51; N, 17.55

EXAMPLE 32

Hydrazinecarboxamide, Carbamic Acid, 2-[3,4-dihydro-3-(1-naphthalenyl)-4-oxo-2-quinazolinyl]-N-(3-methylphenyl)-

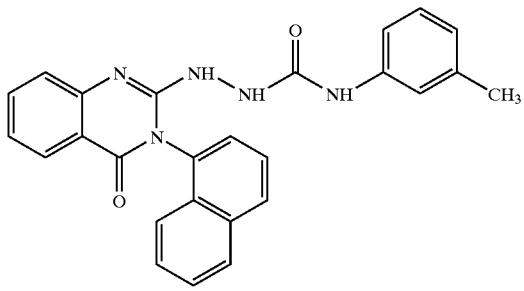

The titled compound was prepared by the method as described for Example 8, but using 2-hydrazino-1-naphthalen-3-yl-3H-quinazolin-4-one. The title compound was isolated as a white solid (0.2 g, 23%) mp 225–227° C.

$C_{26}H_{21}N_5O_2$
Calc.: C, 71.71; H, 4.86; N, 16.08
Found: C, 71.53; H, 4.81; N, 16.19

EXAMPLE 33

HYdrazinecarboxamide, 2-[3,4-dihydro-3-(3-methoxyphenyl)-4-oxo-2-quinazolinyl]-N-(3-methylphenyl)

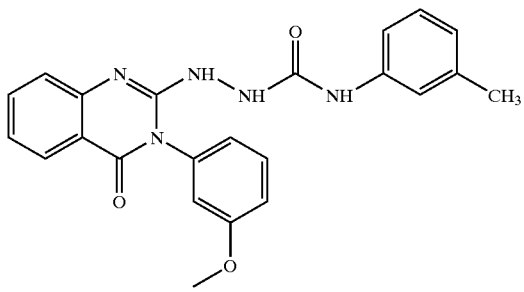

The titled compound was prepared by the method as described for Example 8, but using 2-hydrazino-3-(3-methoxyphenyl)-3H-quinazolin-4-one. the title compound was isolated as a white solid (0.32 g, 77%) mp 193–195° C.

$C_{22}H_{21}N_5O_3$
Calc.: C, 66.49; H, 5.09; N, 16.86
Found: C, 66.33; H, 5.04; N, 16.96

EXAMPLE 34

Hydrazinecarboxamide, 2-[3-[3-(dimethylamino)phenyl]-3,4-dihydro-4-oxo-2-quinazolinyl]-N-(3-methylphenyl)-

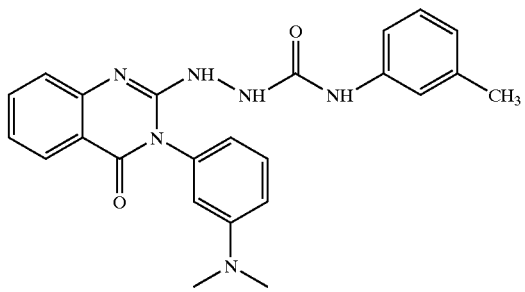

The titled compound was prepared by the method as described for Example 8, but using 3-[3-[3-(dimethylamino)phenyl}-2-hydrazino-3H-quinazolin-4-one. The title compound was isolated as a white solid (0.32 g, 77%) mp 193–195° C.

$C_{24}H_{24}N_6O_2$
Calc.: C, 67.27; H, 5.65; N, 19.61
Found: C, 67.32; H, 5.64; N, 19.64

EXAMPLE 35

Hydrazinecarboxamide, 2-[3,4-dihydro-4-oxo-3-(3-pyridinyl)-2-quinoxalinyl]-N-(3-methylphenyl)-

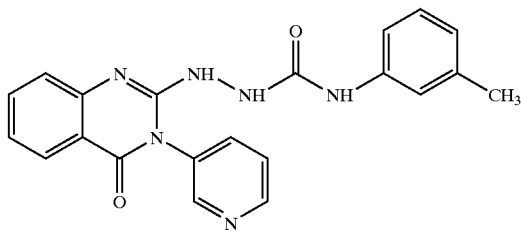

The titled compound was prepared by the method as described for Example 8, but using 2-hydrazino-3-pyridin-3-yl-3H-quinazolin-4-one. The title compound was isolated as a white solid (0.32 g, 77%) mp 193–195° C.

$C_{21}H_{18}N_6O_2$: $0.1H_2O_1$
Calc.: C, 64.97; H, 4.73; N, 21.65
Found: C, 64.65; H, 4.72; N, 21.93

EXAMPLE 36

Hydrazinecarboxamide, 2-[3-(3-aminophenyl)-3,4-dihydro-4-oxo-2-quinazolinyl]-N-(3-methylpheny)-

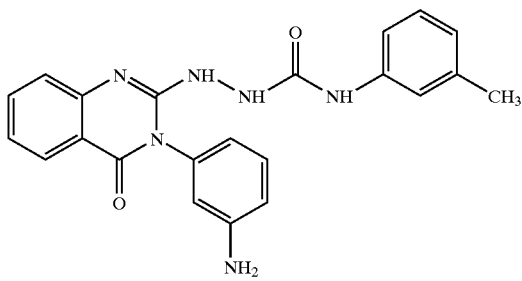

The titled compound was prepared by the method as described for Example 8, but using 3-(3-aminophenyl)-2-hydrazino-3H-quinazolin-4-one. The title compound was isolated as a yellow solid (0.7 g, 62.5%) mp 203–204° C.

$C_{22}H_{20}N_6O_2$
Calc.: C, 65.99; H, 5.03; N, 20.99
Found: C, 65.62, H, 5.08; N, 20.58

EXAMPLE 37

Benzoic Acid, 3-[[[2-[3,4-dihydro-3-[3-(1-methylethoxy)-phenyl]-4-oxo-pyrido[2,3-d]pyrimidin-2-yl]hydrazino]-carbonyl]amino]-, Ethyl Ester

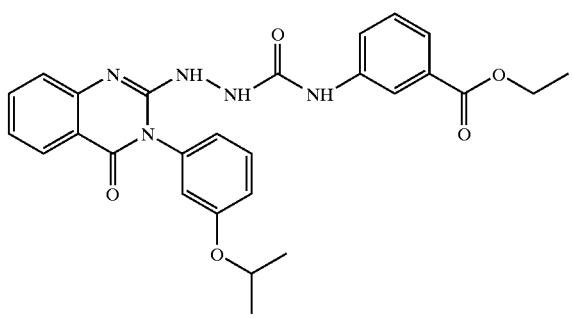

The titled compound was prepared by the method as described for Example 2, but using 2-Hydrazino-3-(3-isopropoxy-phenyl)-3H-pyrido[2,3-d]pyrimidin-4-one. The title compound was isolated as a white solid (0.5, 54.6%) mp 150–160° C.

$C_{26}H_{26}N_6O_5$: $1.0H_2O_1$
Calc.: C, 59.99; H, 5.42; N, 16.14
Found: C, 59.63; H, 5.04; N, 15.86

EXAMPLE 38

Hydrazinecarboxamide, N-(3-cyanophenyl)-2-[3,4-dihydro-3-[3-(dimethylamino)phenyl]-4-oxo-2-quinazolinyl]-

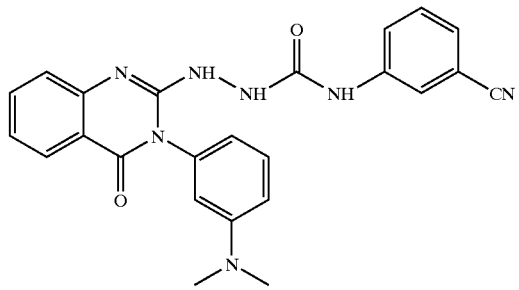

The titled compound was prepared by the method as described for Example 14, but using 3-(3-dimethylaminophenyl)-2-hydrazino-3H-quinazolin-4-one. The title compound was isolated as a white solid (0.48 g, 54.6%) mp 204–205° C.

$C_{26}H_{26}N_6O_5$: $1.0H_2O_1$
Calc.: C, 65.59; H, 4.82; N, 22.31
Found: C, 65.54; H, 4.99; N, 22.00

EXAMPLE 39

Hydrazinecarboxamide, N-(3-cyanophenyl)-2-[3,4-dihydro-4-oxo-3-(3-pyridinyl)-2-quinoxalinyl]-

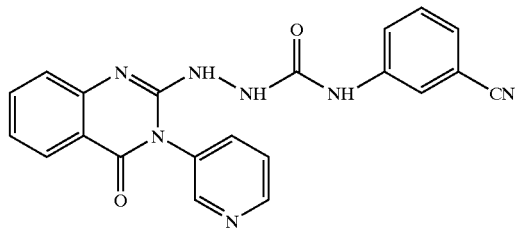

The titled compound was prepared by the method as described for Example 14, but using 2-hydrazino-3-pyridin-3-yl-3H-quinazolin-4-one. The title compound was isolated as a white solid (0.36 g, 91.5%) mp>280° C.

$C_{21}H_{18}N_6O_2$: $0.1H_2O_1$
Calc.: C, 64.97; H, 4.73; N, 21.65
Found: C, 64.65; H, 4.72; N, 21.93

EXAMPLE 40

Hydrazine Carboxamide, 2-[3-(4-chlorophenyl)-3,4-dihydro-4-oxo-2-quinazolinyl]-N-[3-(dimethyl Amino)phenyl]

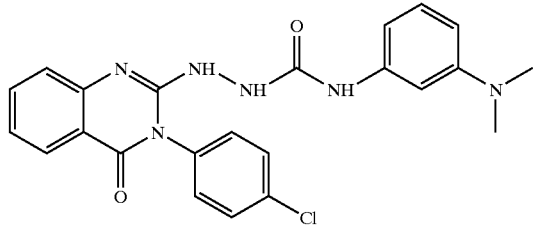

The titled compound was prepared by the method as described for Example 18, but using 3-diaminophenyisocyanate. The title compound was isolated as a white solid (0.23 g, 50.2%) mp 265–267° C.

$C_{23}H_{21}Cl_1N_6O_2$
Calc.: C, 61.54; H, 4.72; N, 18.72; Cl, 7.90
Found: C, 61.17; H, 4.75; N, 18.38; Cl, 7.83

EXAMPLE 41

Benzoic Acid, 3-[[[2-[3,4-dihydro-3-(4-methoxyphenyl)-4-oxo-2-quinazolinyl]hydrazino]carbonyl]amino]-, Ethyl Ester

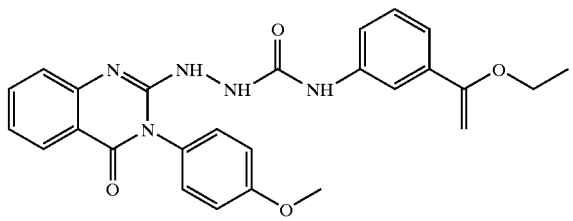

The titled compound was prepared by the method as described for Example 2, but using 2-hydrazino-3-(4-methoxyphenyl)-3H-quinazolin-4-one. The title compound was isolated as a white solid (0.83 g, 87.1%) mp 211–213° C.

$C_{25}H_{23}N_5O_5$
Calc.: C, 63.42; H, 4.90; N, 14.79
Found: C, 63.56; H, 4.95; N, 14.82

EXAMPLE 42

Benzoic Acid, 3-[[[2-[3,4-dihydro-3-(3,4-dimethoxyphenyl)-4-oxo-2-quinazolinyl]hydrazino]carbonyl]amino]-m Ethyl Ester

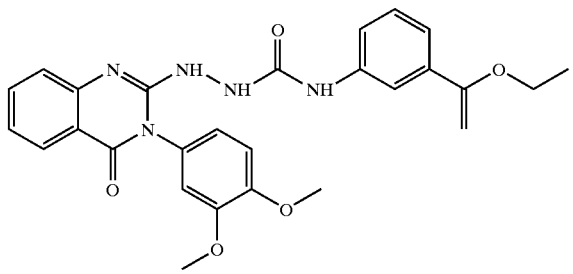

The titled compound was prepared by the method as described for Example 2, but using 3-(3,4-dimethoxyphenyl)-2-hydrazino-3H-quinazolin-4-one. The title compound was isolated as a white solid (0.32 g, 63.3%) mp>280° C.

$C_{26}H_{25}N_5O_6$
Calc.: C, 62.02; H, 5.00; N, 13.91
Found: C, 61.79; H, 5.01; N, 13.91

EXAMPLE 43

Hydrazinecarboxamide, 2-[3-(3,4-dimethoxyphenyl)-3,4-dihydro-4-oxo-2-quinazolinyl]-N-(3-methylphenyl)-

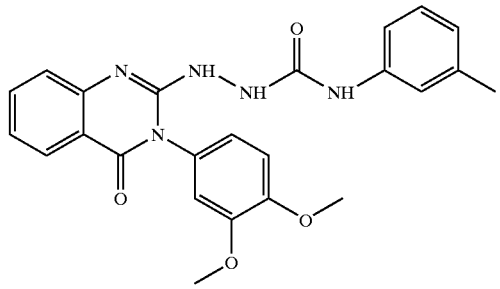

The titled compound was prepared by the method as described for Example 8, but using 3-(3,4-dimethoxyphenyl)-2-hydrazino-3H-quinazolin-4-one. The title compound was isolated as a yellow solid (0.31 g, 69.58%) mp 230–235° C.

$C_{24}H_{23}N_5O_4$
Calc.: C, 64.71; H, 5.20; N, 15.72
Found: C, 64.48; H, 5.36; N, 15.84

EXAMPLE 44

Hydrazinecarboxamide, N-(3,4-dimethoxyphenyl)-2-3,4-dihydro-3-[3-(dimethylamino)phenyl]-4-oxo-2-quinazolin-yl]-

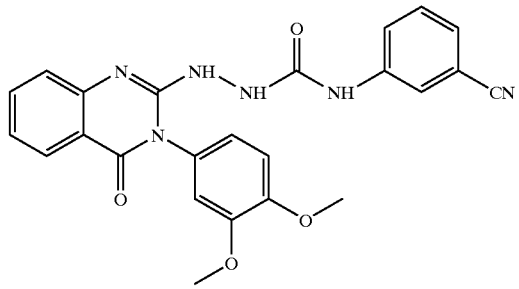

The titled compound was prepared by the method as described for Example 14, but using 3-(3,4-dimethoxyphenyl)-2-hydrazino-3H-quinazolin-4-one. The title compound was isolated as a white solid (0.29 g, 63.53%) mp 206–208° C.

$C_{24}H_{20}N_5O_4$
Calc.: C, 63.15; H, 4.42; N, 18.41
Found: C, 63.10; H, 4.40; N, 18.41

Biological Testing

The following table represents the CCK-A and CCK-B receptor binding affinities of the compounds.

TABLE I

Structure: pyrido-pyrimidinone with X, $R_1$, and NHNH-C(O)-NH-$R_2$ substituents

| No. | X | $R_1$ | $R_2$ | CCK-A (Ki, nM) | CCK-B (Ki, nM) |
|---|---|---|---|---|---|
| 1 | CH | 3-iPrO—Ph | 4-Br—Ph | 3432 | 16.0 |
| 2 | CH | 3-iPrO—Ph | 4-COOEt—Ph | 3296 | 57.2 |
| 3 | CH | 3-iPrO—Ph | 4-CF$_3$—Ph | 2836 | 82.6 |
| 4 | CH | 3-iPrO—Ph | 3-Me—Ph | 7110 | 11.4 |
| 5 | CH | 3-iPrO—Ph | 3,5-Cl$_2$-4-pyridinyl | 5723 | 108.3 |
| 6 | CH | 3-iPrO—Ph | 3-COOEt—Ph | 4430 | 1.7 |
| 7 | CH | 3-iPrO—Ph | 3-COOtBu—Ph | 3576 | 2.0 |
| 8 | CH | 3-iPrO—Ph | 3-COOH—Ph | 8192 | 29.3 |
| 9 | CH | 3-iPrO—Ph | 4-MeO—Ph | 15490 | 25.4 |
| 10 | CH | 3-iPrO—Ph | 3-MeO—Ph | 7603 | 43.9 |
| 11 | CH | 3-iPrO—Ph | 2-MeO—Ph | 4723 | 11.0 |
| 12 | CH | 3-iPrO—Ph | Ph | 5079 | 14.6 |
| 13 | CH | 3-iPrO—Ph | 4-Cl—Ph | 3639 | 12.9 |
| 14 | CH | 3-iPrO—Ph | 3-CN—Ph | 5386 | 1.2 |
| 15 | CH | 3-iPrO—Ph | Cycohexyl | 17667 | 104.7 |
| 16 | CH | 3-iPrO—Ph | 2-COOEt—Ph | 21% @ 10 μM | 6939 |
| 17 | CH | 2-Me—Ph | 3-COOEt—Ph | 4444 | 102.4 |
| 18 | CH | 2-Et—Ph | 3-COOEt—Ph | 5023 | 120.0 |
| 19 | CH | 4-Cl—Ph | 3-COOEt—Ph | 26490 | 11.5 |
| 20 | CH | 3,4-Cl$_2$—Ph | 3-COOEt—Ph | 1756 | 53.4 |
| 21 | CH | 3-F—Ph | 3-COOEt—Ph | 46990 | 25.3 |
| 22 | CH | 1-Naphthyl | 3-COOEt—Ph | 0% @ 10 μM | 23950 |
| 23 | CH | 3-MeO—Ph | 3-COOEt—Ph | 2406 | 15.0 |
| 24 | CH | 3-NH$_2$—Ph | 3-COOEt—Ph | 76.2 | 245 |
| 25 | CH | 3-Cl—Ph | 3-COOEt—Ph | 5056 | 30.0 |
| 26 | CH | 3-NMe$_2$—Ph | 3-COOEt—Ph | 2656 | 5.1 |
| 27 | CH | Morpholine-SO$_2$—Ph | 3-COOEt—Ph | 1583 | 509 |
| 28 | CH | 3-pyridinyl | 3-COOEt—Ph | 10190 | 660 |
| 29 | CH | 4-MeO—Ph | 3-COOEt—Ph | 16% @ 10 μM | 41.5 |
| 30 | CH | 2-Me—Ph | 3-Me—Ph | 6770 | 2590 |
| 31 | CH | 2-Et—Ph | 3-Me—Ph | 5285 | 1011 |
| 32 | CH | 4-Cl—Ph | 3-Me—Ph | 21% @ 10 μM | 405.2 |
| 33 | CH | 2,3-Cl$_2$—Ph | 3-Me—Ph | 3306 | 74.3 |
| 34 | CH | 3-F—Ph | 3-Me—Ph | 32% @ 10 μM | 209 |
| 35 | CH | 1-Naphthyl | 3-Me—Ph | 10% @ 10 μM | 1013 |
| 36 | CH | 3-MeO—Ph | 3-Me—Ph | 9495 | 303.3 |
| 37 | CH | 3-NMe$_2$—Ph | 3-Me—Ph | 4963 | 64.5 |
| 38 | CH | 3-pyridinyl | 3-Me—Ph | 10600 | 4580 |
| 39 | CH | 3-NMe$_2$—Ph | 3-CN—Ph | 5739 | 18.1 |
| 40 | CH | 3-pyridinyl | 3-CN—Ph | — | 637 |
| 41 | N | 3-iPrO—Ph | 3-COOEt—Ph | 6529 | 13395 |

The testing procedures are disclosed in Hays et al, *Neuropeptides* 1:53–62, 1980; and Satuer et al, *Science* 208:1155–1156, 1980.

The compounds described herein are capable of further forming both pharmaceutically acceptable acid addition and/or base salts. All of these forms are within the scope of the present invention.

Pharmaceutically acceptable acid addition salts of the active compounds include salts derived from inorganic acids such as hydrochloric, nitric, phosphoric, sulfuric, hydrobromic, hydriodic, hydrofluoric, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogen-phosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methyl-benzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M. et al., "Pharmaceutical Salts", *JOURNAL OF PHARMACEUTICAL SCIENCE*, 66, pp. 1–19 (1977)).

The acid addition salts of said basic compounds are prepared by contacting the free base form with a sufficient amount of the desired acid to produce the salt in the conventional manner. Preferably, an active compound can be converted to an acidic salt by treating with an aqueous solution of the desired acid, such that the resulting pH is less than 4. The solution can be passed through a C18 cartridge to absorb the compound, washed with copious amounts of water, the compound eluted with a polar organic solvent such as, for example, methanol, acetonitrile, and the like, and isolated by concentrating under reduced pressure followed by lyophilization. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, S. M. et al., "Pharmaceutical Salts", *JOURNAL OF PHARMACEUTICAL SCIENCE,* 66, pp. 1–19 (1977)).

The base addition salts of said acidic compounds are prepared by contacting the free acid form with a sufficient amount of the desired base to produce the salt in the conventional manner. Preferably, an active compound can be converted to a base salt by treating with an aqueous solution of the desired base, such that the resulting pH is greater than 9. The solution can be passed through a C18 cartridge to absorb the compound, washed with copious amounts of water, the compound eluted with a polar organic solvent such as, for example, methanol, acetonitrile and the like, and isolated by concentrating under reduced pressure followed by lyophilization. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

While the forms of the invention herein disclosed constitute presently preferred embodiments, many others are possible. It is not intended herein to mention all of the possible equivalent forms or ramifications of the invention. It is understood that the terms used herein are merely descriptive rather than limiting and that various changes may be made without departing from the spirit or scope of the invention.

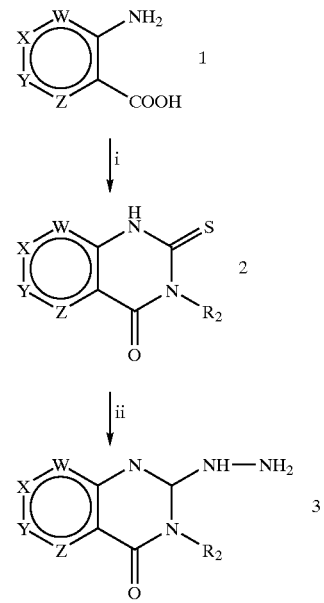

Scheme I

Key: i) $R_2NCS$
ii) $NH_2NH_2$

SCHEME II

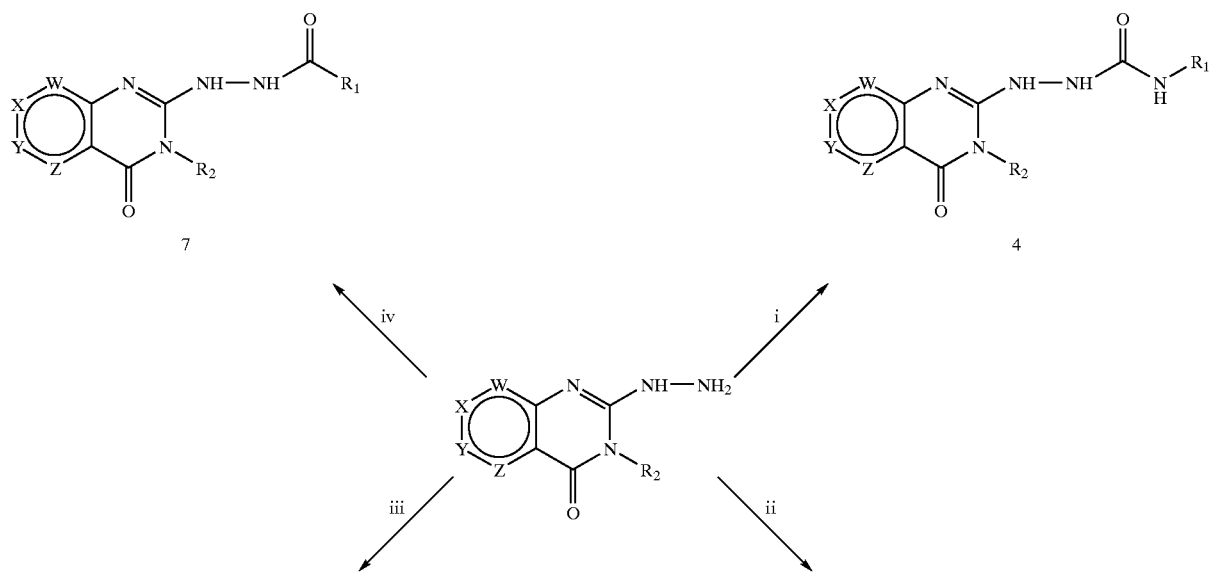

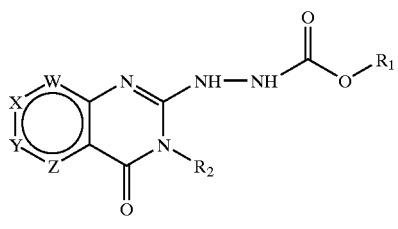

6

Key: i) R₁NCO
ii) R₁NCS
iii) R₁OCOCl
iv) R₁COCl

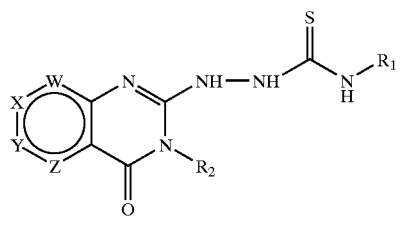

5

What is claimed is:

1. A compound having the structure and meanings for R as indicated:

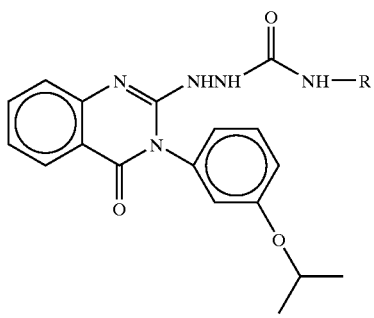

wherein R is selected from the group consisting of:
a) 4-BrPh;
b) 4-COOEt-Ph;
d) 3-Me-Ph;
e) 3-COOEt-Ph;
f) 3-COOtBu-Ph;
g) 3-COOH-Ph;
h) 4-MeO-Ph;
i) 3-MeO-Ph; and
j) 2-MeO-Ph, or a pharmaceutically acceptable salt thereof.

2. A compound selected from:

Hydrazinecarboxamide, N-(4-bromophenyl)-2-[3,4-dihydro-3-[3-(1-methylethoxy)phenyl]-4-oxo-2-quinazolinyl]-;

Benzoic acid, 3-[[[2-[3,4-dihydro-3-[3-(1-methyl-ethoxy)phenyl]-4-oxo-2-quinazolinyl]hydrazino]carbonyl]amino]-ethyl ester;

Hydrazinecarboxamide, 2-[3,4-dihydro-3-[3-(1-methylethoxy)phenyl]-4-oxo-2-quinazolinyl]-N-(4-methoxyphenyl)-;

Hydrazinecarboxamide, 2-[3,4-dihydro-3-[3-(1-methylethoxy)phenyl]-4-oxo-2-quinazolinyl]-N-(3-methoxyphenyl)-;

Hydrazinecarboxamide, 2-[3,4-dihydro-3-[3-(1-methylethoxy)phenyl]-4-oxo-2-quinazolinyl]-N-(2-methoxyphenyl)-;

Hydrazinecarboxamide, 2-(3,4-dihydro-3-(3-(1-methylethoxy)phenyl]-4-oxo-2-quinazolinyl]-N-[(4-trifluoromethyl)phenyl]-;

Benzoic acid, 3-[[[2-[3,4-dihydro-3-[3-(1-methyl-ethoxy)phenyl]-4-oxo-2-quinazolinyl]hydrazino]carbonyl]amino]-, 1,1-dimethylethyl ester;

Hydrazinecarboxamide, 2-[3,4-dihydro-3-[3-(1-methylethoxy)phenyl]-4-oxo-2-quinazolinyl]-N-(3-mathylphenyl)-;

Benzoic acid, 4-[[[2-[3,4-dihydro-3-[3-(1-methyl-ethoxy)phenyl]-4-oxo-2-quinazolinyl]hydrazino]carbonyl]amino]-ethyl ester;

Benzoic acid, 2-[[[2-[3,4-dihydro-3-[3-(1-methyl-ethoxy)phenyl]-4-oxo-2-quinazolinyl]hydrazino]carbonyl]amino]-; ethyl ester;

Benzoic acid, 3-[[[2-[3,4-dihydro-3-[3-(1-methyl-ethoxy)phenyl]-4-oxo-2-quinazolinyl]hydrazino]carbonyl]amino]-; and Benzoic acid, 3-[[[2-[3,4-dihydro-3-[3-(1-methyl-ethoxy)phenyl]-4-oxo-2-quinazolinyl]hydramino]carbonyl]amino]-1,1-dimethylethyl ester, or a pharmaceutically acceptable salt thereof.

3. A pharmaceutically acceptable salt of the compound of claim 1.

4. A pharmaceutically acceptable salt of the compound of claim 2.

5. A pharmaceutical composition comprising the compound of claim 1 or a pharmaceutically acceptable salt thereof and a pharmaceutically acceptable carrier.

6. A pharmaceutical composition comprising the compound of claim 2 or a pharmaceutically acceptable salt thereof and a pharmaceutically acceptable carrier.

7. A method of reducing gastric acid secretion in a mammal comprising administering an effective gastric acid secretion reducing amount to a mammal in need thereof a compound of Formula I:

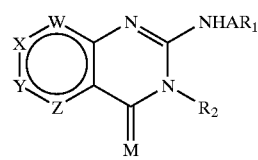

Formula I wherein W, X, Y, and
Z are C—R₃, C—R₄, C—R₅, and C—R₆;
R₃–R₆ are hydrogen;
M is oxygen;
A is

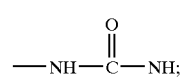

and $R_1$ and $R_2$ are substituted phenyl, wherein
the substitutions are selected from
- hydrogen
- lower alkyl of 1–4 carbon atoms,
- $(CH_2)_iOR_{13}$
- $(CH_2)_iSR_{13}$
- trifluoromethyl
- nitro
- halo
- cyano
- azido
- acetyl

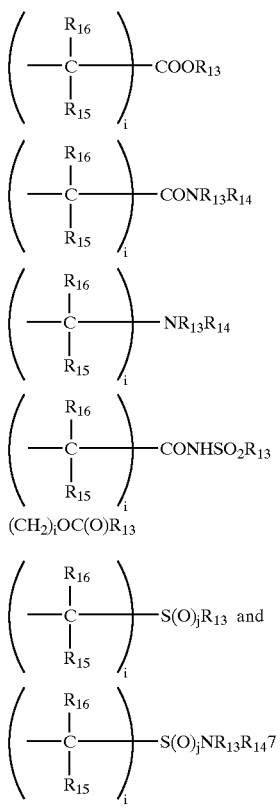

$(CH_2)_iOC(O)R_{13}$ wherein i and j are independently 0, 1, 2, $R_{13}$, $R_{14}$, $R_{15}$, $R_{16}$ are each independently hydrogen, lower alky, alkaryl of from 7 to 10 carbon atoms; and $NR_{13}R_{14}$ is also mono or bicyclic ring with one to four hetero atoms as N,O,S.

8. A method of reducing anxiety in a mammal, comprising administering an effective anxiety reducing amount to a mammal in need thereof a compound of Formula I:

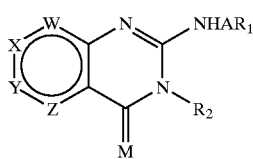

Formula I wherein W, X, Y, and Z are $C—R_3$, $C—R_4$, $C—R_5$, and $C—R_6$;

$R_3$–$R_6$ are hydrogen;

M is oxygen;

A is

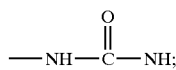

and $R_2$ are substituted phenyl, wherein
the substitutions are selected from
- hydrogen
- lower alkyl of 1–4 carbon atoms,
- $(CH_2)_iOR_{13}$
- $(CH_2)_iSR_{13}$
- trifluoromethyl
- nitro
- halo
- cyano
- azido
- acetyl

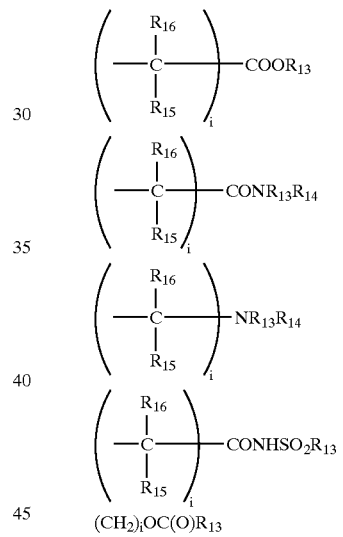

$(CH_2)_iOC(O)R_{13}$

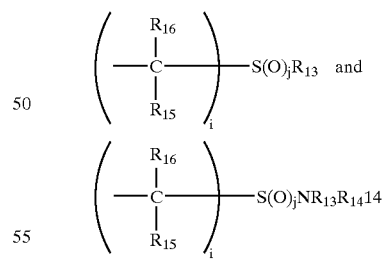

wherein i and j are independently 0, 1, 2, $R_{13}$, $R_{14}$, $R_{15}$, $R_{16}$ are each independently hydrogen, lower alky, alkaryl of from 7 to 10 carbon atoms; and $NR_{13}R_{14}$ is also mono or bicyclic ring with one to four hetero atoms as N,O,S.

9. A method for treating gastrointestinal ulcers in a mammal comprising administering an effective gastrointestinal ulcer treating amount to a mammal in need thereof a compound of Formula I:

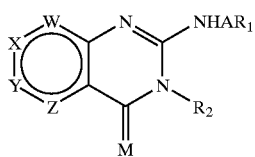

Formula I wherein W, X, Y, and Z are C—R$_3$, C—R$_4$, C—R$_5$, and C—R$_6$;
R$_3$–R$_6$ are hydrogen;
M is oxygen;
A is

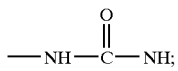

and
R$_1$ and R$_2$ are substituted phenyl, wherein
the substitutions are selected from
  hydrogen
  lower alkyl of 1–4 carbon atoms,
  (CH$_2$)$_i$OR$_{13}$
  (CH$_2$)$_i$SR$_{13}$
  trifluoromethyl
  nitro
  halo
  cyano
  azido
  acetyl

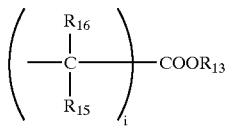

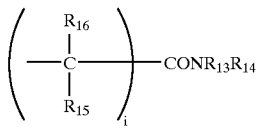

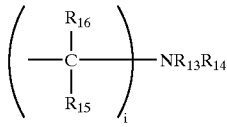

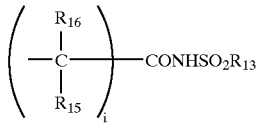

(CH$_2$)$_i$OC(O)R$_{13}$

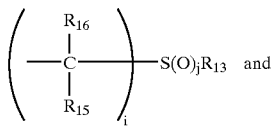

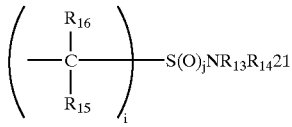

wherein i and j are independently 0, 1, 2, R$_{13}$, R$_{14}$, R$_{15}$, R$_{16}$ are each independently hydrogen, lower alky, alkaryl of from 7 to 10 carbon atoms; and NR$_{13}$R$_{14}$ is also mono or bicyclic ring with one to four hetero atoms an N,O,S.

10. A method of treating psychosis in a mammal comprising administering an effective psychosis in a mammal comprising administering an effective psychosis treating amount to a mammal in need thereof a compound of Formula I:

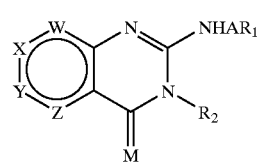

Formula I wherein W, X, Y, and Z are C—R$_3$, C—R$_4$, C—R$_5$, and C—R$_6$;
R$_3$–R$_6$ are hydrogen;
M is oxygen
A is

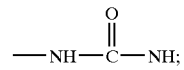

and
R$_1$ and R$_2$ are substituted phenyl, wherein
the substitutions are selected from
  hydrogen
  lower alkyl of 1–4 carbon atoms,
  (CH$_2$)$_i$OR$_{13}$
  (C$_2$)$_i$SR$_{13}$
  trifluoromethyl
  nitro
  halo
  cyano
  azido
  acetyl

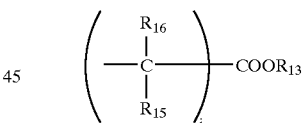

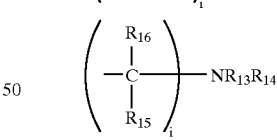

(CH$_2$)$_i$OC(O)R$_{13}$

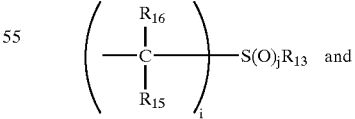

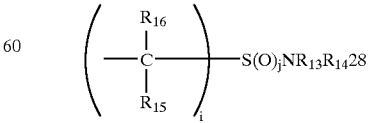

wherein i and j are independently 0, 1, 2, R$_{13}$, R$_{14}$, R$_{15}$, R$_{16}$ are each independently hydrogen, lower alky, alkaryl of from 7 to 10 carbon atoms; and NR$_{13}$R$_{14}$ is also mono or bicyclic ring with one to four hetero atoms as N,O,S.

11. A method of treating pain in a mammal comprising administering an effective amount to a mammal in need thereof a compound of Formula I:

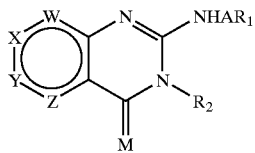

Formula I wherein wherein

W, X, Y, and Z are C—R$_3$, C—R$_4$, C—R$_5$, and C—R$_6$;

R$_3$–R$_6$ are hydrogen;

M is oxygen;

A is

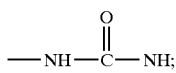

and

R$_1$ and R$_2$ are substituted phenyl, wherein the substitutents are selected from
  hydrogen
  lower alkyl of 1–4 carbon atoms,
  (CH$_2$)$_i$OR$_{13}$
  (CH$_2$)$_i$SR$_{13}$
  trifluoromethyl
  nitro
  halo
  cyano
  azido
  acetyl

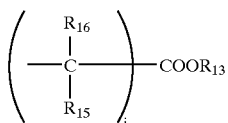 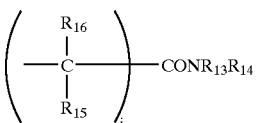

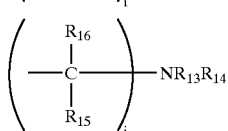 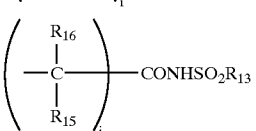

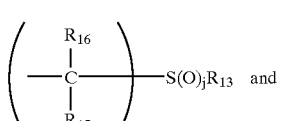

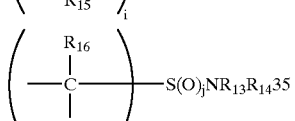

wherein i and j are independently 0, 1, 2, R$_{13}$, R$_{14}$, R$_{15}$, R$_{16}$ are each independently hydrogen, lower alky, alkaryl of from 7 to 10 carbon atom; and NR$_{13}$R$_{14}$ is also mono or bicyclic ring with one to four hetero atoms as N,O,S.

12. A method of treating panic in a mammal comprising administering an effective amount to a mammal in need thereof a compound of Formula I:

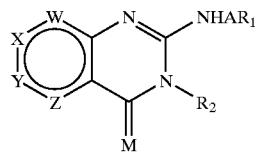

Formula I wherein W, X, y, and Z are C—R$_3$, C—R$_4$, C—R$_5$, and C—R$_6$;

R$_3$–R$_6$ are hydrogen;

M is oxygen;

A is

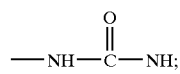

and

R$_1$ and R$_2$ are substituted phenyl, wherein the substitutions are selected from
  hydrogen
  lower alkyl of 1–4 carbon atoms,
  (CH$_2$)$_i$OR$_{13}$
  trifluoromethyl
  nitro
  halo
  cyano
  azido
  acetyl

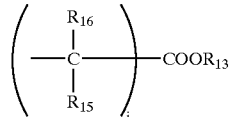 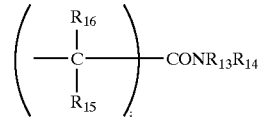

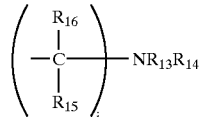 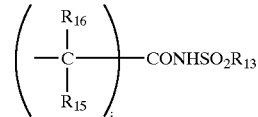

  and

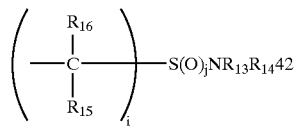

wherein i and j are independently 0, 1, 2, R$_{13}$, R$_{14}$, R$_{15}$, R$_{16}$ are each independently hydrogen, lower alky, alkaryl of from 7 to 10 carbon atoms; and NR$_{13}$R$_{14}$ is also mono or bicyclic ring with one to four hetero atoms as N,O,S.

* * * * *